(12) United States Patent
Hofmann et al.

(10) Patent No.: US 11,078,472 B2
(45) Date of Patent: Aug. 3, 2021

(54) RECOMBINANT CLOSTRIDIAL NEUROTOXINS WITH INCREASED DURATION OF EFFECT

(71) Applicant: Merz Pharma GmbH & Co. KGaA, Frankfurt am Main (DE)

(72) Inventors: Fred Hofmann, Potsdam (DE); Marcel Jurk, Berlin (DE); Manuela López De La Paz, Liederbach am Taunus (DE); Daniel Scheps, Potsdam (DE); Jürgen Frevert, Berlin (DE)

(73) Assignee: Merz Pharma GmbH & Co., KGaA, Frankfurt am Main (DE)

( * ) Notice: Subject to any disclaimer, the term of this patent is extended or adjusted under 35 U.S.C. 154(b) by 180 days.

(21) Appl. No.: 15/778,112

(22) PCT Filed: Jan. 19, 2017

(86) PCT No.: PCT/EP2017/051074
§ 371 (c)(1),
(2) Date: Nov. 9, 2018

(87) PCT Pub. No.: WO2017/125487
PCT Pub. Date: Jul. 27, 2017

(65) Prior Publication Data
US 2018/0327730 A1      Nov. 15, 2018

(30) Foreign Application Priority Data

Jan. 20, 2016   (EP) .................................. 16000124

(51) Int. Cl.
*C12N 9/52*      (2006.01)
*C07K 14/33*     (2006.01)
*A61K 38/00*     (2006.01)

(52) U.S. Cl.
CPC ................ *C12N 9/52* (2013.01); *C07K 14/33* (2013.01); *C12Y 304/24069* (2013.01); *A61K 38/00* (2013.01)

(58) Field of Classification Search
None
See application file for complete search history.

(56) References Cited

U.S. PATENT DOCUMENTS

2002/0127247 A1    9/2002   Steward et al.

FOREIGN PATENT DOCUMENTS

| WO | WO 96/39166 A1    | 12/1996 |
| WO | WO 02/08268 A2    | 1/2002  |
| WO | WO 08/08268 A2    | 1/2002  |
| WO | WO 2008/155134 A1 | 12/2008 |
| WO | WO 2011/144756 A1 | 11/2011 |
| WO | WO 2015/132004 A1 | 9/2015  |

OTHER PUBLICATIONS

Alexei et al., "Polyproline-II Helix in Proteins: Structure and Function", *J. Mol. Biol.*, 425, 2100-2132, 2013.
International Search Report and Written Opinion regarding International Application No. PCT/EP2017/051074, dated Apr. 6, 2017.
Adzhubei et al., "Polyproline-II Helix in Proteins: Structure and Function", *J. Mol. Biol.*, 425, 2100-2132, 2013.
Fernández-Salas et al., "Plasma Membrane Localization Signals in the Light Chain of Botulinum Neurotoxin", *PNAS*, 101(9), 3208-3213, 2004.
Wang et al., "A Dileucine in the Protease of Botulinum Toxin A Underlies Its Long-lived Neuroparalysis", *J. Biol Chem*, 286(8):6375-6385, 2011.

*Primary Examiner* — Brian Gangle
(74) *Attorney, Agent, or Firm* — Dentons US LLP

(57) ABSTRACT

This invention relates to novel recombinant clostridial neurotoxins exhibiting increased duration of effect and to methods for the manufacture of such recombinant clostridial neurotoxins. These novel recombinant clostridial neurotoxins comprise (i) at least two random coil domains, or (ii) at least two domains having a polyproline II helix conformation, and the methods comprise the steps of inserting at least two nucleic acid sequences each coding for (i) a random coil domain, or (ii) a domain having a polyproline II helix conformation, into a nucleic acid sequence coding for a parental clostridial neurotoxin and expression of the recombinant nucleic acid sequence comprising (i) the random coil domain-coding sequences, or (ii) the sequences encoding the domains having a polyproline II helix conformation in a host cell. The invention further relates to novel recombinant single-chain precursor clostridial neurotoxins used in such methods, nucleic acid sequences encoding such recombinant single-chain precursor clostridial neurotoxins, and pharmaceutical compositions comprising the recombinant clostridial neurotoxin with increased duration of effect.

17 Claims, 4 Drawing Sheets

Figure 1:
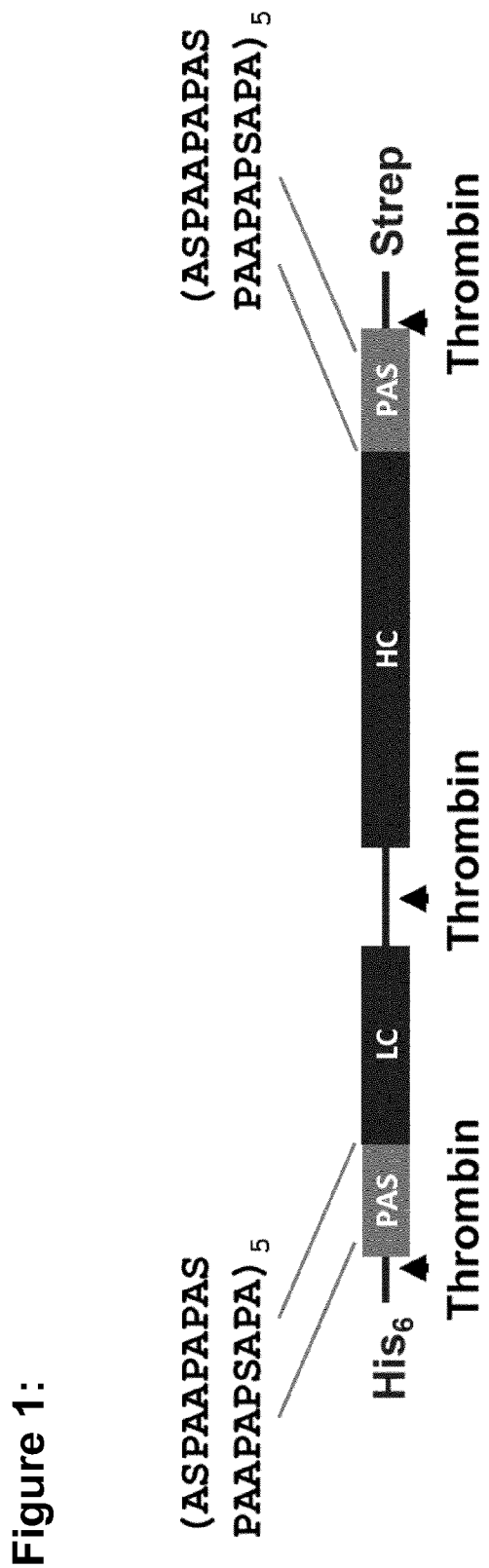

Specification includes a Sequence Listing.

Figure 2:

(A)

(B)

(C)

SEQUENCE LISTING

```
<160> NUMBER OF SEQ ID NOS: 19

<210> SEQ ID NO 1
<211> LENGTH: 20
<212> TYPE: PRT
<213> ORGANISM: Artificial Sequence
<220> FEATURE:
<223> OTHER INFORMATION: PAS20 sequence_I

<400> SEQUENCE: 1

Ala Ser Pro Ala Ala Pro Ala Pro Ala Ser Pro Ala Ala Pro Ala Pro
1               5                   10                  15

Ser Ala Pro Ala
            20
```

```
<210> SEQ ID NO 2
<211> LENGTH: 20
<212> TYPE: PRT
<213> ORGANISM: Artificial Sequence
<220> FEATURE:
<223> OTHER INFORMATION: PAS20 sequence_II

<400> SEQUENCE: 2

Ala Ala Pro Ala Ser Pro Ala Pro Ala Ala Pro Ser Ala Pro Ala Pro
 1               5                  10                  15

Ala Ala Pro Ser
            20

<210> SEQ ID NO 3
<211> LENGTH: 20
<212> TYPE: PRT
<213> ORGANISM: Artificial Sequence
<220> FEATURE:
<223> OTHER INFORMATION: PAS20 sequence_III

<400> SEQUENCE: 3

Ala Pro Ser Ser Pro Ser Pro Ser Ala Pro Ser Ser Pro Ser Pro Ala
 1               5                  10                  15

Ser Pro Ser Ser
            20

<210> SEQ ID NO 4
<211> LENGTH: 20
<212> TYPE: PRT
<213> ORGANISM: Artificial Sequence
<220> FEATURE:
<223> OTHER INFORMATION: PAS20 sequence_IV

<400> SEQUENCE: 4

Ser Ala Pro Ser Ser Pro Ser Pro Ser Ala Pro Ser Pro Ser Pro
 1               5                  10                  15

Ala Ser Pro Ser
            20

<210> SEQ ID NO 5
<211> LENGTH: 20
<212> TYPE: PRT
<213> ORGANISM: Artificial Sequence
<220> FEATURE:
<223> OTHER INFORMATION: PAS20 sequence_V

<400> SEQUENCE: 5

Ser Ser Pro Ser Ala Pro Ser Pro Ser Ser Pro Ala Pro Ser Pro
 1               5                  10                  15

Ser Ser Pro Ala
            20

<210> SEQ ID NO 6
<211> LENGTH: 24
<212> TYPE: PRT
<213> ORGANISM: Artificial Sequence
<220> FEATURE:
<223> OTHER INFORMATION: PAS24 sequence_I

<400> SEQUENCE: 6

Ala Ala Ser Pro Ala Ala Pro Ser Ala Pro Pro Ala Ala Ala Ser Pro
 1               5                  10                  15

Ala Ala Pro Ser Ala Pro Pro Ala
            20
```

```
<210> SEQ ID NO 7
<211> LENGTH: 20
<212> TYPE: PRT
<213> ORGANISM: Artificial Sequence
<220> FEATURE:
<223> OTHER INFORMATION: PAS20 sequence_VI

<400> SEQUENCE: 7

Ala Ser Ala Ala Ala Pro Ala Ala Ala Ser Ala Ala Ala Ser Ala Pro
1               5                   10                  15

Ser Ala Ala Ala
            20

<210> SEQ ID NO 8
<211> LENGTH: 1504
<212> TYPE: PRT
<213> ORGANISM: Artificial Sequence
<220> FEATURE:
<223> OTHER INFORMATION: recombinant PAS100-rBoNT/A-PAS100 (amino acid
      sequence)

<400> SEQUENCE: 8

Ser Ser Ala Ser Pro Ala Ala Pro Ala Pro Ala Ser Pro Ala Ala Pro
1               5                   10                  15

Ala Pro Ser Ala Pro Ala Ala Ser Pro Ala Ala Pro Ala Pro Ala Ser
                20                  25                  30

Pro Ala Ala Pro Ala Pro Ser Ala Ala Pro Ala Ala Ser Pro Ala Ala Pro
                35                  40                  45

Ala Pro Ala Ser Pro Ala Ala Pro Ala Pro Ser Ala Pro Ala Ala Ser
            50                  55                  60

Pro Ala Ala Pro Ala Pro Ala Ser Pro Ala Ala Pro Ala Pro Ser Ala
65                  70                  75                  80

Pro Ala Ala Ser Pro Ala Ala Pro Ala Pro Ser Pro Ala Ala Pro
                85                  90                  95

Ala Pro Ser Ala Pro Ala Ala Pro Phe Val Asn Lys Gln Phe Asn Tyr
                100                 105                 110

Lys Asp Pro Val Asn Gly Val Asp Ile Ala Tyr Ile Lys Ile Pro Asn
                115                 120                 125

Ala Gly Gln Met Gln Pro Val Lys Ala Phe Lys Ile His Asn Lys Ile
            130                 135                 140

Trp Val Ile Pro Glu Arg Asp Thr Phe Thr Asn Pro Glu Glu Gly Asp
145                 150                 155                 160

Leu Asn Pro Pro Glu Ala Lys Gln Val Pro Val Ser Tyr Tyr Asp
                165                 170                 175

Ser Thr Tyr Leu Ser Thr Asp Asn Glu Lys Asp Asn Tyr Leu Lys Gly
            180                 185                 190

Val Thr Lys Leu Phe Glu Arg Ile Tyr Ser Thr Asp Leu Gly Arg Met
            195                 200                 205

Leu Leu Thr Ser Ile Val Arg Gly Ile Pro Phe Trp Gly Gly Ser Thr
            210                 215                 220

Ile Asp Thr Glu Leu Lys Val Ile Asp Thr Asn Cys Ile Asn Val Ile
225                 230                 235                 240

Gln Pro Asp Gly Ser Tyr Arg Ser Glu Glu Leu Asn Leu Val Ile Ile
                245                 250                 255

Gly Pro Ser Ala Asp Ile Ile Gln Phe Glu Cys Lys Ser Phe Gly His
                260                 265                 270

Glu Val Leu Asn Leu Thr Arg Asn Gly Tyr Gly Ser Thr Gln Tyr Ile
```

```
            275                 280                 285
Arg Phe Ser Pro Asp Phe Thr Phe Gly Phe Glu Glu Ser Leu Glu Val
290                 295                 300

Asp Thr Asn Pro Leu Leu Gly Ala Gly Lys Phe Ala Thr Asp Pro Ala
305                 310                 315                 320

Val Thr Leu Ala His Glu Leu Ile His Ala Gly His Arg Leu Tyr Gly
                    325                 330                 335

Ile Ala Ile Asn Pro Asn Arg Val Phe Lys Val Asn Thr Asn Ala Tyr
                340                 345                 350

Tyr Glu Met Ser Gly Leu Glu Val Ser Phe Glu Glu Leu Arg Thr Phe
            355                 360                 365

Gly Gly His Asp Ala Lys Phe Ile Asp Ser Leu Gln Glu Asn Glu Phe
        370                 375                 380

Arg Leu Tyr Tyr Tyr Asn Lys Phe Lys Asp Ile Ala Ser Thr Leu Asn
385                 390                 395                 400

Lys Ala Lys Ser Ile Val Gly Thr Thr Ala Ser Leu Gln Tyr Met Lys
                    405                 410                 415

Asn Val Phe Lys Glu Lys Tyr Leu Leu Ser Glu Asp Thr Ser Gly Lys
                420                 425                 430

Phe Ser Val Asp Lys Leu Lys Phe Asp Lys Leu Tyr Lys Met Leu Thr
            435                 440                 445

Glu Ile Tyr Thr Glu Asp Asn Phe Val Lys Phe Lys Val Leu Asn
        450                 455                 460

Arg Lys Thr Tyr Leu Asn Phe Asp Lys Ala Val Phe Lys Ile Asn Ile
465                 470                 475                 480

Val Pro Lys Val Asn Tyr Thr Ile Tyr Asp Gly Phe Asn Leu Arg Asn
                    485                 490                 495

Thr Asn Leu Ala Ala Asn Phe Asn Gly Gln Asn Thr Glu Ile Asn Asn
                500                 505                 510

Met Asn Phe Thr Lys Leu Lys Asn Phe Thr Gly Leu Phe Glu Phe Tyr
            515                 520                 525

Lys Leu Leu Cys Val Arg Gly Ile Ile Thr Ser Lys Ala Gly Ala Gly
        530                 535                 540

Lys Ser Leu Val Pro Arg Gly Ser Ala Gly Ala Gly Ala Leu Asn Asp
545                 550                 555                 560

Leu Cys Ile Lys Val Asn Asn Trp Asp Leu Phe Phe Ser Pro Ser Glu
                    565                 570                 575

Asp Asn Phe Thr Asn Asp Leu Asn Lys Gly Glu Glu Ile Thr Ser Asp
                580                 585                 590

Thr Asn Ile Glu Ala Ala Glu Glu Asn Ile Ser Leu Asp Leu Ile Gln
            595                 600                 605

Gln Tyr Tyr Leu Thr Phe Phe Asp Asn Glu Pro Glu Asn Ile Ser
        610                 615                 620

Ile Glu Asn Leu Ser Ser Asp Ile Ile Gly Gln Leu Glu Leu Met Pro
625                 630                 635                 640

Asn Ile Glu Arg Phe Pro Asn Gly Lys Lys Tyr Glu Leu Asp Lys Tyr
                    645                 650                 655

Thr Met Phe His Tyr Leu Arg Ala Gln Glu Phe Glu His Gly Lys Ser
                660                 665                 670

Arg Ile Ala Leu Thr Asn Ser Val Asn Glu Ala Leu Leu Asn Pro Ser
            675                 680                 685

Arg Val Tyr Thr Phe Phe Ser Ser Asp Tyr Val Lys Lys Val Asn Lys
        690                 695                 700
```

```
Ala Thr Glu Ala Ala Met Phe Leu Gly Trp Val Gln Leu Val Tyr
705                 710                 715                 720

Asp Phe Thr Asp Glu Thr Ser Glu Val Ser Thr Thr Asp Lys Ile Ala
            725                 730                 735

Asp Ile Thr Ile Ile Ile Pro Tyr Ile Gly Pro Ala Leu Asn Ile Gly
        740                 745                 750

Asn Met Leu Tyr Lys Asp Asp Phe Val Gly Ala Leu Ile Phe Ser Gly
        755                 760                 765

Ala Val Ile Leu Leu Glu Phe Ile Pro Glu Ile Ala Ile Pro Val Leu
770                 775                 780

Gly Thr Phe Ala Leu Val Ser Tyr Ile Ala Asn Lys Val Leu Thr Val
785                 790                 795                 800

Gln Thr Ile Asp Asn Ala Leu Ser Lys Arg Asn Glu Lys Trp Asp Glu
            805                 810                 815

Val Tyr Lys Tyr Ile Val Thr Asn Trp Leu Ala Lys Val Asn Thr Gln
            820                 825                 830

Ile Asp Leu Ile Arg Lys Lys Met Lys Glu Ala Leu Glu Asn Gln Ala
        835                 840                 845

Glu Ala Thr Lys Ala Ile Ile Asn Tyr Gln Tyr Asn Gln Tyr Thr Glu
850                 855                 860

Glu Glu Lys Asn Asn Ile Asn Phe Asn Ile Asp Asp Leu Ser Ser Lys
865                 870                 875                 880

Leu Asn Glu Ser Ile Asn Lys Ala Met Ile Asn Ile Asn Lys Phe Leu
            885                 890                 895

Asn Gln Cys Ser Val Ser Tyr Leu Met Asn Ser Met Ile Pro Tyr Gly
        900                 905                 910

Val Lys Arg Leu Glu Asp Phe Asp Ala Ser Leu Lys Asp Ala Leu Leu
        915                 920                 925

Lys Tyr Ile Tyr Asp Asn Arg Gly Thr Leu Ile Gly Gln Val Asp Arg
    930                 935                 940

Leu Lys Asp Lys Val Asn Asn Thr Leu Ser Thr Asp Ile Pro Phe Gln
945                 950                 955                 960

Leu Ser Lys Tyr Val Asp Asn Gln Arg Leu Leu Ser Thr Phe Thr Glu
            965                 970                 975

Tyr Ile Lys Asn Ile Ile Asn Thr Ser Ile Leu Asn Leu Arg Tyr Glu
        980                 985                 990

Ser Asn His Leu Ile Asp Leu Ser Arg Tyr Ala Ser Lys Ile Asn Ile
        995                 1000                1005

Gly Ser Lys Val Asn Phe Asp Pro Ile Asp Lys Asn Gln Ile Gln
    1010                1015                1020

Leu Phe Asn Leu Glu Ser Ser Lys Ile Glu Val Ile Leu Lys Asn
    1025                1030                1035

Ala Ile Val Tyr Asn Ser Met Tyr Glu Asn Phe Ser Thr Ser Phe
    1040                1045                1050

Trp Ile Arg Ile Pro Lys Tyr Phe Asn Ser Ile Ser Leu Asn Asn
    1055                1060                1065

Glu Tyr Thr Ile Ile Asn Cys Met Glu Asn Asn Ser Gly Trp Lys
    1070                1075                1080

Val Ser Leu Asn Tyr Gly Glu Ile Ile Trp Thr Leu Gln Asp Thr
    1085                1090                1095

Gln Glu Ile Lys Gln Arg Val Val Phe Lys Tyr Ser Gln Met Ile
    1100                1105                1110
```

-continued

```
Asn Ile Ser Asp Tyr Ile Asn Arg Trp Ile Phe Val Thr Ile Thr
1115                1120                1125

Asn Asn Arg Leu Asn Asn Ser Lys Ile Tyr Ile Asn Gly Arg Leu
1130                1135                1140

Ile Asp Gln Lys Pro Ile Ser Asn Leu Gly Asn Ile His Ala Ser
1145                1150                1155

Asn Asn Ile Met Phe Lys Leu Asp Gly Cys Arg Asp Thr His Arg
1160                1165                1170

Tyr Ile Trp Ile Lys Tyr Phe Asn Leu Phe Asp Lys Glu Leu Asn
1175                1180                1185

Glu Lys Glu Ile Lys Asp Leu Tyr Asp Asn Gln Ser Asn Ser Gly
1190                1195                1200

Ile Leu Lys Asp Phe Trp Gly Asp Tyr Leu Gln Tyr Asp Lys Pro
1205                1210                1215

Tyr Tyr Met Leu Asn Leu Tyr Asp Pro Asn Lys Tyr Val Asp Val
1220                1225                1230

Asn Asn Val Gly Ile Arg Gly Tyr Met Tyr Leu Lys Gly Pro Arg
1235                1240                1245

Gly Ser Val Met Thr Thr Asn Ile Tyr Leu Asn Ser Ser Leu Tyr
1250                1255                1260

Arg Gly Thr Lys Phe Ile Ile Lys Lys Tyr Ala Ser Gly Asn Lys
1265                1270                1275

Asp Asn Ile Val Arg Asn Asn Asp Arg Val Tyr Ile Asn Val Val
1280                1285                1290

Val Lys Asn Lys Glu Tyr Arg Leu Ala Thr Asn Ala Ser Gln Ala
1295                1300                1305

Gly Val Glu Lys Ile Leu Ser Ala Leu Glu Ile Pro Asp Val Gly
1310                1315                1320

Asn Leu Ser Gln Val Val Val Met Lys Ser Lys Asn Asp Gln Gly
1325                1330                1335

Ile Thr Asn Lys Cys Lys Met Asn Leu Gln Asp Asn Asn Gly Asn
1340                1345                1350

Asp Ile Gly Phe Ile Gly Phe His Gln Phe Asn Asn Ile Ala Lys
1355                1360                1365

Leu Val Ala Ser Asn Trp Tyr Asn Arg Gln Ile Glu Arg Ser Ser
1370                1375                1380

Arg Thr Leu Gly Cys Ser Trp Glu Phe Ile Pro Val Asp Asp Gly
1385                1390                1395

Trp Gly Glu Arg Pro Leu Ala Ser Pro Ala Ala Pro Ala Pro Ala
1400                1405                1410

Ser Pro Ala Ala Pro Ala Pro Ser Ala Pro Ala Ala Ser Pro Ala
1415                1420                1425

Ala Pro Ala Pro Ala Ser Pro Ala Ala Pro Ala Pro Ser Ala Pro
1430                1435                1440

Ala Ala Ser Pro Ala Ala Pro Ala Pro Ala Ser Pro Ala Ala Pro
1445                1450                1455

Ala Pro Ser Ala Pro Ala Ala Ser Pro Ala Ala Pro Ala Pro Ala
1460                1465                1470

Ser Pro Ala Ala Pro Ala Pro Ser Ala Pro Ala Ala Ser Pro Ala
1475                1480                1485

Ala Pro Ala Pro Ala Ser Pro Ala Ala Pro Ala Pro Ser Ala Pro
1490                1495                1500

Ala
```

<210> SEQ ID NO 9
<211> LENGTH: 4512
<212> TYPE: DNA
<213> ORGANISM: Artificial Sequence
<220> FEATURE:
<223> OTHER INFORMATION: recombinant PAS100-rBoNT/A-PAS100 (DNA sequence)

<400> SEQUENCE: 9
tcttctgcaa gtccggcagc accggcaccg gcttcaccag ctgcaccagc acctagcgca 60
ccggcagcat ctccagcagc ccctgcaccg gcaagccctg cagctccagc accgtcagca 120
ccagcagcaa gcccagctgc tcctgctcca gcgagcccag cagcgccagc tcctagtgcc 180
cctgctgcct ctcctgctgc tccggcacca gcaagtcctg ctgcgcctgc accgagtgct 240
ccggctgcta gtcctgccgc accagctccg gctagtccag ctgctccagc cccttcagcc 300
cctgcagcac catttgtgaa caagcagttt aactataagg acccggtgaa cggtgtggat 360
atcgcgtata tcaaaatccc gaatgcgggc cagatgcaac cagtcaaggc gttcaagatt 420
cataacaaga tttgggttat tccggaacgt gataccttca ccaatccgga agaaggcgat 480
ttaaatccgc cgccagaagc caaacaagtg ccggtgagct actatgatag cacgtatctt 540
agcaccgata atgaaaaaga caattacctg aagggcgtga ccaagttgtt cgagcgcatc 600
tacagtaccg acttaggccg catgttgttg acgagcatcg ttcgcggtat cccgttctgg 660
ggcggctcga ccattgatac cgagttgaaa gtcattgaca cgaactgtat caatgttatc 720
caaccggacg gcagttatcg cagcgaggag ttaaatttgg tcatcatcgg tccaagcgca 780
gatattattc agttcgaatg caagagcttc ggccatgagg tcttgaattt gacgcgcaac 840
ggttacggca gcacccaata catccgcttt agcccggatt tcacctttgg cttcgaggag 900
agcttggagg tggacaccaa cccgctgtta ggtgccggca aattcgcaac cgacccggca 960
gtgacgttgg cgcacgaatt gattcatgcg ggtcaccgct tatacggtat cgcgatcaat 1020
ccgaatcgcg tctttaaagt caataccaac gcgtactacg aaatgagcgg cttagaggtt 1080
agctttgaag aattacgcac cttcggtggc cacgacgcca agttcatcga cagcctgcag 1140
gaaaatgagt tccgcttgta ctattacaat aaattcaagg acatcgcgag caccttaaat 1200
aaagcaaaga gcattgtggg caccaccgca agcttgcagt acatgaagaa cgtatttaag 1260
gaaaaatatt tgttgtcgga ggataccagc gggaaattca gcgtcgataa gctgaaattc 1320
gacaaattgt ataaaatgct gaccgagatt tacaccgagg ataacttcgt caagtttttt 1380
aaggtgttaa atcgtaagac ctatttaaac tttgataaag cggtgtttaa aattaatatc 1440
gtgccgaagg tgaattacac catctacgat ggtttcaatt tacgcaacac gaatctggcg 1500
gcgaatttta atggccaaaa caccgaaatt aacaacatga actttacgaa gttaaagaat 1560
ttcacgggct tattcgaatt ctacaagtta ttatgcgtgc gcggcatcat taccagcaag 1620
gcaggtgcgg gcaagtcctt ggttccgcgt ggcagcgccg gcgccggcgc gctcaatgat 1680
ctgtgtatta aagtcaataa ctgggacctg ttcttcagcc cgagcgagga taactttacc 1740
aacgacttaa acaaaggcga ggagatcacg agcgatacga acatcgaggc ggcggaggaa 1800
aatattagcc tggacctcat tcagcagtac tatctgacgt tcaattttga caatgagccg 1860
gagaacatca gcattgaaaa tctcagcagc gacatcatcg gtcagttgga actgatgccg 1920
aacattgaac gctttccgaa cggcaaaaaa tatgaactgg acaagtatac catgttccat 1980
tacttacgcg cacaggaatt tgagcacggc aagagccgca ttgcgctgac caatagcgtt 2040

```
aacgaggcct tgttaaatcc gagccgtgtc tacacgttct tcagcagcga ttatgtcaaa    2100
aaagtgaaca aggcgaccga agccgcgatg tttttgggct gggtcgagca attggtttac    2160
gattttaccg acgaaaccag cgaggtgagc acgaccgaca aaattgcaga tatcaccatc    2220
atcattccgt acatcggtcc ggcgctcaat atcggcaata tgttatacaa ggacgacttt    2280
gtgggcgcgc tgatctttag cggcgcggtt atcttattag aattcatccc ggagatcgca    2340
atcccggtct tgggcacctt tgcgttggtg agctatatcg cgaataaagt gctcacggtc    2400
caaaccatcg ataacgcgct cagcaagcgt aatgagaaat gggacgaggt ttataagtat    2460
atcgtgacca actggttagc aaaagtcaat acgcagatcg atctcatccg caaaaaaatg    2520
aaagaagcct tggaaaatca agcggaggca accaaagcca tcattaatta ccagtataac    2580
caatataccg aagaagaaaa aaacaatatc aacttcaata tcgatgattt gagcagcaaa    2640
ctgaacgaga gcattaacaa agcgatgatt aacatcaaca agttcttgaa tcaatgcagc    2700
gtgagctatc tcatgaacag catgatcccg tatggcgtca aacgcttgga agattttgac    2760
gccagcctga agatgcgct cctcaagtat atttatgaca accgcggcac cctcattggc    2820
caggtggacc gcttgaagga taaagtgaac aatacgctca gcacggatat cccgttccag    2880
ctgagcaagt acgtcgacaa ccagcgctta ctgagcacct ttaccgagta tatcaagaac    2940
atcattaata ccagcatcct caacttgcgc tatgagagca atcacctgat cgacctcagc    3000
cgctacgcca gcaagatcaa catcggcagc aaggtcaatt tcgacccgat cgataagaat    3060
cagatccaat tgtttaacct ggaaagcagc aagatcgagg ttatcttgaa gaacgcgatt    3120
gtgtacaaca gcatgtacga aactttagc acgagcttct ggattcgtat cccgaagtat    3180
ttcaatagca ttagcctgaa taacgaatat accattatca actgcatgga aaataatagc    3240
ggctggaagg tgagcttaaa ttacggcgag atcatttgga ccttacagga tacccaagaa    3300
atcaaacagc gcgtcgtctt taagtatagc cagatgatca acatcagcga ttacatcaac    3360
cgctggatct tcgtgaccat caccaataat cgcttgaata atagcaagat ttacatcaat    3420
ggtcgcttga ttgatcaaaa accgatcagc aatctcggta atatccatgc cagcaataac    3480
atcatgttta agttagacgg ttgccgcgat acccaccgct atatctggat caagtatttt    3540
aacttatttg ataaggaact caacgaaaag gaaattaaag acttatatga caatcagagc    3600
aatagcggca tcctgaagga tttctggggc gactacctgc agtacgataa gccgtactat    3660
atgttgaact tgtatgaccc gaacaaatat gtcgatgtga acaatgtggg tattcgtggc    3720
tatatgtact taaagggccc gcgtggtagc gtgatgacca cgaatattta cttaaacagc    3780
agcttatacc gcggcacgaa gtttattatc aagaagtatg ccagcggcaa caaggacaat    3840
atcgtccgca caacgaccg tgtgtatatt aacgtggtgg tgaagaataa agagtaccgc    3900
ttggccacga atgcgagcca ggcgggcgtg aaaaaatct tgagcgcgtt ggagatcccg    3960
gacgtcggca acctcagcca ggttgtggtg atgaagtcta aaaacgacca gggcatcacg    4020
aacaagtgca aaatgaattt gcaagataac aacggcaacg catcggctt tattggtttt    4080 caccagttca ataacatcgc caaactcgtg ccagcaatt ggtataaccg ccaaattgaa    4140
cgcagcagcc gcacgctcgg ctgtagctgg gagttcatcc cggtggacga tggctggggc    4200
gagcgcccgc tcgcaagtcc ggcagcaccg gcaccggctt caccagctgc accagcacct    4260
agcgcaccgg cagcatctcc agcagcccct gcaccggcaa gccctgcagc tccagcaccg    4320
tcagcaccag cagcaagccc agctgctcct gctccagcga gcccagcagc gccagctcct    4380
```

```
agtgccctg ctgcctctcc tgctgctccg gcaccagcaa gtcctgctgc gcctgcaccg    4440
agtgctccgg ctgctagtcc tgccgcacca gctccggcta gtccagctgc tccagcccct    4500
tcagcccctg ca                                                         4512
```

```
<210> SEQ ID NO 10
<211> LENGTH: 20
<212> TYPE: PRT
<213> ORGANISM: Artificial Sequence
<220> FEATURE:
<223> OTHER INFORMATION: PAS60 to PAS500: (ASPAAPAPASPAAPAPSAPA)n, with
      n being an integer selected from 3 to 25
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 3 to 25

<400> SEQUENCE: 10

Ala Ser Pro Ala Ala Pro Ala Pro Ala Ser Pro Ala Ala Pro Ala Pro
1               5                   10                  15

Ser Ala Pro Ala
            20

<210> SEQ ID NO 11
<211> LENGTH: 20
<212> TYPE: PRT
<213> ORGANISM: Artificial Sequence
<220> FEATURE:
<223> OTHER INFORMATION: PAS80 to PAS160: (ASPAAPAPASPAAPAPSAPA)n, with
      n being an integer selected from 4 to 8
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 4 to 8

<400> SEQUENCE: 11

Ala Ser Pro Ala Ala Pro Ala Pro Ala Ser Pro Ala Ala Pro Ala Pro
1               5                   10                  15

Ser Ala Pro Ala
            20

<210> SEQ ID NO 12
<211> LENGTH: 20
<212> TYPE: PRT
<213> ORGANISM: Artificial Sequence
<220> FEATURE:
<223> OTHER INFORMATION: PAS100 to PAS200: (ASPAAPAPASPAAPAPSAPA)n, with
      n being an integer selected from 5 to 10
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 5 to 10

<400> SEQUENCE: 12

Ala Ser Pro Ala Ala Pro Ala Pro Ala Ser Pro Ala Ala Pro Ala Pro
1               5                   10                  15

Ser Ala Pro Ala
            20

<210> SEQ ID NO 13
<211> LENGTH: 100
<212> TYPE: PRT
<213> ORGANISM: Artificial Sequence
<220> FEATURE:
<223> OTHER INFORMATION: PAS100: (ASPAAPAPASPAAPAPSAPA)n, with n being 5
```

```
<400> SEQUENCE: 13

Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
                20                  25                  30

Ala Pro Ala Pro Ser Ala Pro Ala Ala Ser Pro Ala Ala Pro Ala Pro
            35                  40                  45

Ala Ser Pro Ala Ala Pro Ala Pro Ser Ala Pro Ala Ala Ser Pro Ala
        50                  55                  60

Ala Pro Ala Pro Ala Ser Pro Ala Ala Pro Ala Pro Ser Ala Pro Ala
65                  70                  75                  80

Ala Ser Pro Ala Ala Pro Ala Pro Ala Ser Pro Ala Ala Pro Ala Pro
            85                  90                  95

Ser Ala Pro Ala
            100

<210> SEQ ID NO 14
<211> LENGTH: 200
<212> TYPE: PRT
<213> ORGANISM: Artificial Sequence
<220> FEATURE:
<223> OTHER INFORMATION: PAS200: (ASPAAPAPASPAAPAPSAPA)n, with n being
      10

<400> SEQUENCE: 14

Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
                20                  25                  30

Ala Pro Ala Pro Ser Ala Pro Ala Ala Ser Pro Ala Ala Pro Ala Pro
            35                  40                  45

Ala Ser Pro Ala Ala Pro Ala Pro Ser Ala Pro Ala Ala Ser Pro Ala
        50                  55                  60

Ala Pro Ala Pro Ala Ser Pro Ala Ala Pro Ala Pro Ser Ala Pro Ala
65                  70                  75                  80

Ala Ser Pro Ala Ala Pro Ala Pro Ala Ser Pro Ala Ala Pro Ala Pro
            85                  90                  95

Ser Ala Pro Ala Ala Ser Pro Ala Ala Pro Ala Pro Ala Ser Pro Ala
            100                 105                 110

Ala Pro Ala Pro Ser Ala Pro Ala Ala Ser Pro Ala Ala Pro Ala Pro
        115                 120                 125

Ala Ser Pro Ala Ala Pro Ala Pro Ser Ala Pro Ala Ala Ser Pro Ala
    130                 135                 140

Ala Pro Ala Pro Ala Ser Pro Ala Ala Pro Ala Pro Ser Ala Pro Ala
145                 150                 155                 160

Ala Ser Pro Ala Ala Pro Ala Pro Ala Ser Pro Ala Ala Pro Ala Pro
            165                 170                 175

Ser Ala Pro Ala Ala Ser Pro Ala Ala Pro Ala Pro Ser Pro Ala
            180                 185                 190

Ala Pro Ala Pro Ser Ala Pro Ala
        195                 200

<210> SEQ ID NO 15
<211> LENGTH: 20
<212> TYPE: PRT
<213> ORGANISM: Artificial Sequence
```

```
<220> FEATURE:
<223> OTHER INFORMATION: PAS100 to PAS3000: (ASPAAPAPASPAAPAPSAPA)n,
      with n being an integer selected from 5 to 150
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 5 to 150

<400> SEQUENCE: 15

Ala Ser Pro Ala Ala Pro Ala Pro Ala Ser Pro Ala Ala Pro Ala Pro
1               5                   10                  15

Ser Ala Pro Ala
            20

<210> SEQ ID NO 16
<211> LENGTH: 20
<212> TYPE: PRT
<213> ORGANISM: Artificial Sequence
<220> FEATURE:
<223> OTHER INFORMATION: PAS120 to PAS400: (ASPAAPAPASPAAPAPSAPA)n, with
      n being an integer selected from 6 to 20
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 6 to 20

<400> SEQUENCE: 16

Ala Ser Pro Ala Ala Pro Ala Pro Ala Ser Pro Ala Ala Pro Ala Pro
1               5                   10                  15

Ser Ala Pro Ala
            20

<210> SEQ ID NO 17
<211> LENGTH: 20
<212> TYPE: PRT
<213> ORGANISM: Artificial Sequence
<220> FEATURE:
<223> OTHER INFORMATION: PAS140 to PAS260: (ASPAAPAPASPAAPAPSAPA)n, with
      n being an integer selected from 7 to 13
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 7 to 13

<400> SEQUENCE: 17

Ala Ser Pro Ala Ala Pro Ala Pro Ala Ser Pro Ala Ala Pro Ala Pro
1               5                   10                  15

Ser Ala Pro Ala
            20

<210> SEQ ID NO 18
<211> LENGTH: 20
<212> TYPE: PRT
<213> ORGANISM: Artificial Sequence
<220> FEATURE:
<223> OTHER INFORMATION: PAS160 to PAS240: (ASPAAPAPASPAAPAPSAPA)n, with
      n being an integer selected from 8 to 12
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 8 to 12

<400> SEQUENCE: 18

Ala Ser Pro Ala Ala Pro Ala Pro Ala Ser Pro Ala Ala Pro Ala Pro
1               5                   10                  15
```

```
Ser Ala Pro Ala
            20

<210> SEQ ID NO 19
<211> LENGTH: 20
<212> TYPE: PRT
<213> ORGANISM: Artificial Sequence
<220> FEATURE:
<223> OTHER INFORMATION: PAS180 to PAS220: (ASPAAPAPASPAAPAPSAPA)n, with
      n being an integer selected from 9 to 11
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 9 to 11

<400> SEQUENCE: 19

Ala Ser Pro Ala Ala Pro Ala Pro Ala Ser Pro Ala Ala Pro Ala Pro
1               5                   10                  15

Ser Ala Pro Ala
            20
```

RECOMBINANT CLOSTRIDIAL NEUROTOXINS WITH INCREASED DURATION OF EFFECT

CROSS-REFERENCE TO RELATED APPLICATIONS

This application is a 371 National Stage application of International Application No. PCT/EP2017/051074, filed Jan. 19, 2017, which claims the benefit of application no. EP16000124.4, filed Jan. 20, 2016, and is herein incorporated by reference in its entirety.

INCORPORATION OF SEQUENCE LISTING BY REFERENCE

The sequence listing contained in the file named "WRST006US_ST25.txt", which is 28 kilobytes (size as measured in Microsoft Windows®) and was created on May 14, 2018, is filed herewith by electronic submission and is incorporated by reference herein.

FIELD OF THE INVENTION

This invention relates to novel recombinant clostridial neurotoxins exhibiting increased duration of effect and to methods for the manufacture of such recombinant clostridial neurotoxins. These novel recombinant clostridial neurotoxins comprise (i) at least two random coil domains, or (ii) at least two domains having a polyproline II helix conformation, and the methods comprise the steps of inserting at least two nucleic acid sequences each coding for (i) a random coil domain, or (ii) a domain having a polyproline II helix conformation, into a nucleic acid sequence coding for a parental clostridial neurotoxin and expression of the recombinant nucleic acid sequence comprising (i) the random coil domain-coding sequences, or (ii) the sequences encoding the domains having a polyproline II helix conformation in a host cell. The invention further relates to novel recombinant single-chain precursor clostridial neurotoxins used in such methods, nucleic acid sequences encoding such recombinant single-chain precursor clostridial neurotoxins, and pharmaceutical compositions comprising the recombinant clostridial neurotoxin with increased duration of effect.

BACKGROUND OF THE INVENTION

*Clostridium* is a genus of anaerobe gram-positive bacteria, belonging to the Firmicutes. *Clostridium* consists of around 100 species that include common free-living bacteria as well as important pathogens, such as *Clostridium botulinum* and *Clostridium tetani*. Both species produce neurotoxins, botulinum toxin and tetanus toxin, respectively. These neurotoxins are potent inhibitors of calcium-dependent neurotransmitter secretion of neuronal cells and are among the strongest toxins known to man. The lethal dose in humans lies between 0.1 ng and 1 ng per kilogram of body weight.

Oral ingestion of botulinum toxin via contaminated food or generation of botulinum toxin in wounds can cause botulism, which is characterized by paralysis of various muscles. Paralysis of the breathing muscles can cause death of the affected individual.

Although both botulinum neurotoxin (BoNT) and tetanus neurotoxin (TxNT) function via a similar initial physiological mechanism of action, inhibiting neurotransmitter release from the axon of the affected neuron into the synapse, they differ in their clinical response. While the botulinum toxin acts at the neuromuscular junction and other cholinergic synapses in the peripheral nervous system, inhibiting the release of the neurotransmitter acetylcholine and thereby causing flaccid paralysis, the tetanus toxin acts mainly in the central nervous system, preventing the release of the inhibitory neurotransmitters GABA (gamma-aminobutyric acid) and glycine by degrading the protein synaptobrevin. The consequent overactivity in the muscles results in generalized contractions of the agonist and antagonist musculature, termed a tetanic spasm (rigid paralysis).

While the tetanus neurotoxin exists in one immunologically distinct type, the botulinum neurotoxins are known to occur in seven different immunogenic types, termed BoNT/A through BoNT/H. Most *Clostridium botulinum* strains produce one type of neurotoxin, but strains producing multiple toxins have also been described.

Botulinum and tetanus neurotoxins have highly homologous amino acid sequences and show a similar domain structure. Their biologically active form comprises two peptide chains, a light chain of about 50 kDa and a heavy chain of about 100 kDa, linked by a disulfide bond. A linker or loop region, whose length varies among different clostridial toxins, is located between the two cysteine residues forming the disulfide bond. This loop region is proteolytically cleaved by an unknown clostridial endoprotease to obtain the biologically active toxin.

The molecular mechanism of intoxication by TxNT and BoNT appears to be similar as well: entry into the target neuron is mediated by binding of the C-terminal part of the heavy chain to a specific cell surface receptor; the toxin is then taken up by receptor-mediated endocytosis. The low pH in the so formed endosome then triggers a conformational change in the clostridial toxin which allows it to embed itself in the endosomal membrane and to translocate through the endosomal membrane into the cytoplasm, where the disulfide bond joining the heavy and the light chain is reduced. The light chain can then selectively cleave so called SNARE-proteins, which are essential for different steps of neurotransmitter release into the synaptic cleft, e.g. recognition, docking and fusion of neurotransmitter-containing vesicles with the plasma membrane. TxNT, BoNT/B, BoNT/D, BoNT/F, and BoNT/G cause proteolytic cleavage of synaptobrevin or VAMP (vesicle-associated membrane protein), BoNT/A and BoNT/E cleave the plasma membrane-associated protein SNAP-25, and BoNT/C cleaves the integral plasma membrane protein syntaxin and SNAP-25.

Clostridial neurotoxins display variable durations of action that are serotype specific. The clinical therapeutic effect of BoNT/A lasts approximately 3 months for neuromuscular disorders and 6 to 12 months for hyperhidrosis. The effects of BoNT/E, on the other hand, last less than 4 weeks. The longer lasting therapeutic effect of BoNT/A makes it preferable for clinical use compared to the other serotypes, for example serotypes B, $C_1$, D, E, F, G and H. One possible explanation for the divergent durations of action might be the distinct subcellular localizations of BoNT serotypes. The protease domain of BoNT/A light chain localizes in a punctate manner to the plasma membrane of neuronal cells, co-localizing with its substrate SNAP-25. In contrast, the short-duration BoNT/E serotype is cytoplasmic. Membrane association might protect BoNT/A from cytosolic degradation mechanisms allowing for prolonged persistence of BoNT/A in the neuronal cell.

In *Clostridium botulinum*, the botulinum toxin is formed as a protein complex comprising the neurotoxic component and non-toxic proteins. The accessory proteins embed the neurotoxic component thereby protecting it from degradation by digestive enzymes in the gastrointestinal tract. Thus, botulinum neurotoxins of most serotypes are orally toxic. Complexes with, for example, 500 kDa or with 900 kDa are obtainable from cultures of *Clostridium botulinum* Type A.

In recent years, botulinum neurotoxins have been used as therapeutic agents in the treatment of dystonias and spasms. Preparations comprising botulinum toxin complexes are commercially available, e.g. from Ipsen Ltd (Dysport®) or Allergan Inc. (Botox®). A high purity neurotoxic component, free of any complexing proteins, is for example available from Merz Pharmaceuticals GmbH, Frankfurt (Xeomin®).

Clostridial neurotoxins are usually injected into the affected muscle tissue, bringing the agent close to the neuromuscular end plate, i.e. close to the cellular receptor mediating its uptake into the nerve cell controlling said affected muscle. Various degrees of neurotoxin spread have been observed. The neurotoxin spread is thought to depend on the injected amount and the particular neurotoxin preparation. It can result in adverse side effects such as paralysis in nearby muscle tissue, which can largely be avoided by reducing the injected doses to the therapeutically relevant level. Overdosing can also trigger the immune system to generate neutralizing antibodies that inactivate the neurotoxin preventing it from relieving the involuntary muscle activity. Immunologic tolerance to botulinum toxin has been shown to correlate with cumulative doses and short injection intervals.

At present, clostridial neurotoxins are still predominantly produced by fermentation processes using appropriate *Clostridium* strains. However, industrial production of clostridial neurotoxin from anaerobic *Clostridium* culture is a cumbersome and time-consuming process. Due to the high toxicity of the final product, the procedure must be performed under strict containment. During the fermentation process, the single-chain precursors are proteolytically cleaved by an unknown clostridial protease to obtain the biologically active di-chain clostridial neurotoxin. The degree of neurotoxin activation by proteolytic cleavage varies between different strains and neurotoxin serotypes, which is a major consideration for the manufacture due to the requirement of neurotoxin preparations with a well-defined biological activity. Furthermore, during fermentation processes using *Clostridium* strains the clostridial neurotoxins are produced as protein complexes, in which the neurotoxic component is embedded by accessory proteins. These accessory proteins have no beneficial effect on biological activity, spread of the neurotoxin or duration of effect. They can however trigger an immune reaction in the patient, resulting in immunity against the clostridial neurotoxin leading to secondary nonresponse. Manufacture of recombinant clostridial neurotoxins, which are not embedded by auxiliary proteins, might therefore be advantageous.

Methods for the recombinant expression of clostridial neurotoxins in *E. coli* are well known in the art (see, for example, WO 00/12728, WO 01/14570, or WO 2006/076902). Furthermore, clostridial neurotoxins have been expressed in eukaryotic expression systems, such as in *Pichia pastoris*, *Pichia methanolica*, *Saccharomyces cerevisiae*, insect cells and mammalian cells (see WO 2006/017749).

Recombinant clostridial neurotoxins may be expressed as single-chain precursors, which subsequently have to be proteolytically cleaved to obtain the final biologically active clostridial neurotoxin. Thus, clostridial neurotoxins may be expressed in high yield in rapidly-growing bacteria as relatively non-toxic single-chain polypeptides.

Furthermore, it might be advantageous to modify clostridial neurotoxin characteristics regarding biological activity, cell specificity, antigenic potential and duration of effect by genetic engineering to obtain recombinant neurotoxins with new therapeutic properties in specific clinical areas. Genetic modification of clostridial neurotoxins might allow altering the mode of action or expanding the range of therapeutic targets.

WO 96/39166 discloses analogues of botulinum toxin comprising amino acid residues which are more resistant to degradation in neuromuscular tissue.

Patent family based on WO 02/08268 (including family member U.S. Pat. No. 6,903,187) discloses a clostridial neurotoxin comprising a structural modification selected from addition or deletion of a leucine-based motif, which alters the biological persistence of the neurotoxin (see also: Fernandez-Salas et al., Proc. Natl. Acad. Sci. U.S.A. 101 (2004) 3208-3213; Wang et al., J. Biol. Chem. 286 (2011) 6375-6385). Fernandez-Salas et al. initially hypothesized that the increased persistence was due to the membrane-binding properties of the dileucine motif (see Fernandez-Salas et al., loc. cit., p. 3211 and 3213). Wang et al. mention this membrane theory (see Wang et al., loc. cit., p. 6376, left column, last full paragraph, and p. 6383, first full paragraph of "Discussion"), but favor an alternative theory: the protection from degradation by proteolysis (see Wang et al., loc. cit., p. 6384, left column, lines 27 ff).

US 2002/0127247 describes clostridial neurotoxins comprising modifications in secondary modification sites and exhibiting altered biological persistence.

WO 2015/132004 describes clostridial neurotoxins comprising a random coil domain, particularly wherein said random coil domain consists of alanine, serine and proline residues, and exhibiting an altered biological persistence.

Botulinum toxin variants exhibiting longer biological half lives in neuromuscular tissue than naturally occurring botulinum toxins would be advantageous in order to reduce administration frequency and the incidence of neutralizing antibody generation since immunologic tolerance to botulinum toxin is correlated with cumulative doses.

Furthermore, BoNT serotypes naturally exhibiting a short duration of action could potentially be effectively used in clinical applications, if their biological persistence could be enhanced. Modified BoNT/E with an increased duration of action could potentially be used in patients exhibiting an immune reaction against BoNT/A. Moreover, BoNT/E was shown to induce a more severe block of pain mediator release from sensory neurons than BoNT/A. In clinical applications where BoNT/A provides only partial pain relief or in just a subset of patients, such as in the treatment of headaches, or where BoNT/E has been found to be more effective than BoNT/A but gives only short-term therapy, such as in the treatment of epilepsy, BoNT/E with an increased duration of effect might prove useful.

There is a strong demand to produce clostridial neurotoxins with an increased duration of effect, in order to allow for reduction of administration frequency and exploitation of the therapeutic potential of BoNT serotypes, which have so far been considered impractical for clinical application due to the short half-life of the respective clinically relevant effect. Ideally, the duration of effect of a particular clostridial neurotoxin could be adjusted in a tailor-made fashion in order to address any particular features and demands of a given indication, such as the amount of neurotoxin being administered, frequency of administration etc. To date, despite the progress that has already been made (see, in particular, WO 2015/132004), such aspects have not been solved satisfactorily.

OBJECTS OF THE INVENTION

It was an object of the invention to provide recombinant clostridial neurotoxins exhibiting an increased duration of effect and to establish a reliable and accurate method for manufacturing and obtaining such recombinant clostridial neurotoxins. Such a method and novel precursor clostridial neurotoxins used in such methods would serve to satisfy the great need for recombinant clostridial neurotoxins exhibiting an increased duration of effect.

SUMMARY OF THE INVENTION

The naturally occurring botulinum toxin serotypes display highly divergent durations of effect, probably due to their distinct subcellular localization. BoNT/A exhibiting the longest persistence was shown to localize in the vicinity of the plasma membrane of neuronal cells, whereas the short-duration BoNT/E serotype is cytosolic. However, additional factors such as degradation, diffusion, and/or translocation rates might have a decisive impact on the differences in the duration of effect for the individual botulinum toxin serotypes.

So far, except for the approach described and claimed in WO 2015/132004, no generally applicable method for modifying clostridial neurotoxins in order to increase their duration of effect is available. Surprisingly, it has been found that recombinant clostridial neurotoxins having even better effects than those disclose in WO 2015/132004 can be obtained by cloning two sequences each encoding (i) a random coil domain, or (ii) encoding a domain having a polyproline II helix conformation, into a gene encoding a parental clostridial neurotoxin, and by subsequent heterologous expression of the generated construct in recombinant host cells.

Thus, in one aspect, the present invention relates to recombinant clostridial neurotoxin comprising at least two separate random coil domains.

In an alternative aspect, the present invention relates to recombinant clostridial neurotoxin comprising at least two domains having a polyproline II helix conformation.

In another aspect, the present invention relates to a pharmaceutical composition comprising the recombinant clostridial neurotoxin of the present invention.

In yet another aspect, the present invention relates to the use of the composition comprising the recombinant clostridial neurotoxin of the present invention for the treatment of a patient.

In yet another aspect, the present invention relates to a method for treating a patient comprising the step of administering a composition comprising the recombinant clostridial neurotoxin of the present invention.

In another aspect, the present invention relates to a method for the generation of the recombinant clostridial neurotoxin of the present invention, comprising the step of obtaining a recombinant nucleic acid sequence encoding a recombinant single-chain precursor clostridial neurotoxin by the insertion of one or more nucleic acid sequences each encoding a random coil domain at at least two positions into a nucleic acid sequence encoding a parental clostridial neurotoxin.

In another aspect, the present invention relates to a method for the generation of the recombinant clostridial neurotoxin of the present invention, comprising the step of obtaining a recombinant nucleic acid sequence encoding a recombinant single-chain precursor clostridial neurotoxin by the insertion of one or more nucleic acid sequences each encoding a domain having a polyproline II helix conformation at at least two positions into a nucleic acid sequence encoding a parental clostridial neurotoxin.

In another aspect, the present invention relates to a recombinant single-chain precursor clostridial neurotoxin comprising at least two separate random coil domains.

In another aspect, the present invention relates to a recombinant single-chain precursor clostridial neurotoxin comprising at least two separate domains having a polyproline II helix conformation.

In another aspect, the present invention relates to a nucleic acid sequence encoding the recombinant single-chain precursor clostridial neurotoxin of the present invention.

In another aspect, the present invention relates to a method for obtaining the nucleic acid sequence of the present invention, comprising the step of inserting one or more nucleic acid sequences each encoding a random coil domain at at least two positions into a nucleic acid sequence encoding a parental clostridial neurotoxin.

In another aspect, the present invention relates to a method for obtaining the nucleic acid sequence of the present invention, comprising the step of inserting one or more nucleic acid sequences each encoding a domain having a polyproline II helix conformation at at least two positions into a nucleic acid sequence encoding a parental clostridial neurotoxin.

In another aspect, the present invention relates to a vector comprising the nucleic acid sequence of the present invention, or the nucleic acid sequence obtainable by the method of the present invention.

In another aspect, the present invention relates to a recombinant host cell comprising the nucleic acid sequence of the present invention, the nucleic acid sequence obtainable by the method of the present invention, or the vector of the present invention.

In another aspect, the present invention relates to a method for producing the recombinant single-chain precursor clostridial neurotoxin of the present invention, comprising the step of expressing the nucleic acid sequence of the present invention, or the nucleic acid sequence obtainable by the method of the present invention, or the vector of the present invention in a recombinant host cell, or cultivating the recombinant host cell of the present invention under conditions that result in the expression of said nucleic acid sequence.

FIGURES

FIG. 1: Schematic Presentation of Bis-PASylated Botulinum Toxin A (PAS-rBoNT/A-PAS), wherein PAS corresponds to the 100 mer sequence (ASPAAPAPASPAAPAP-SAPA)$_5$ (SEQ ID NO: 13).

Figure 2:
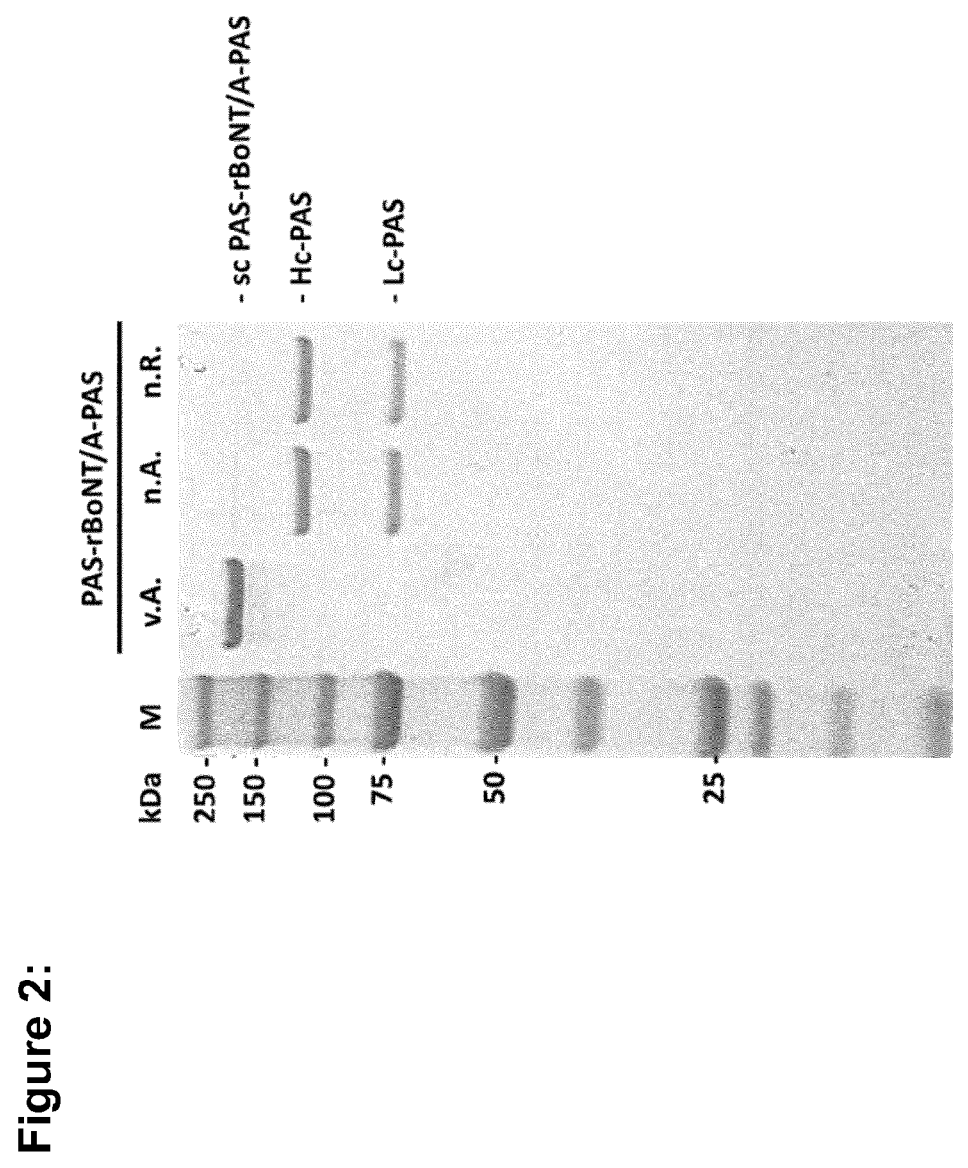

FIG. 2: SDS.PAGE of purified PAS-rBoNT/A-PAS. Prior to applying the samples to the gel, β-mercaptoethanol was added. Lane "v.A.": purified, non-activated single-chain PAS-rBoNT/A-PAS having a molecular weight (Mw) of about 170 kDa. Lanes "n.A." (after activation) and "n.R." (after purification) show light chain (PAS-Lc) and heavy chain (Hc-PAS) obtained after activation by thrombin under reducing conditions.

Figure 3:
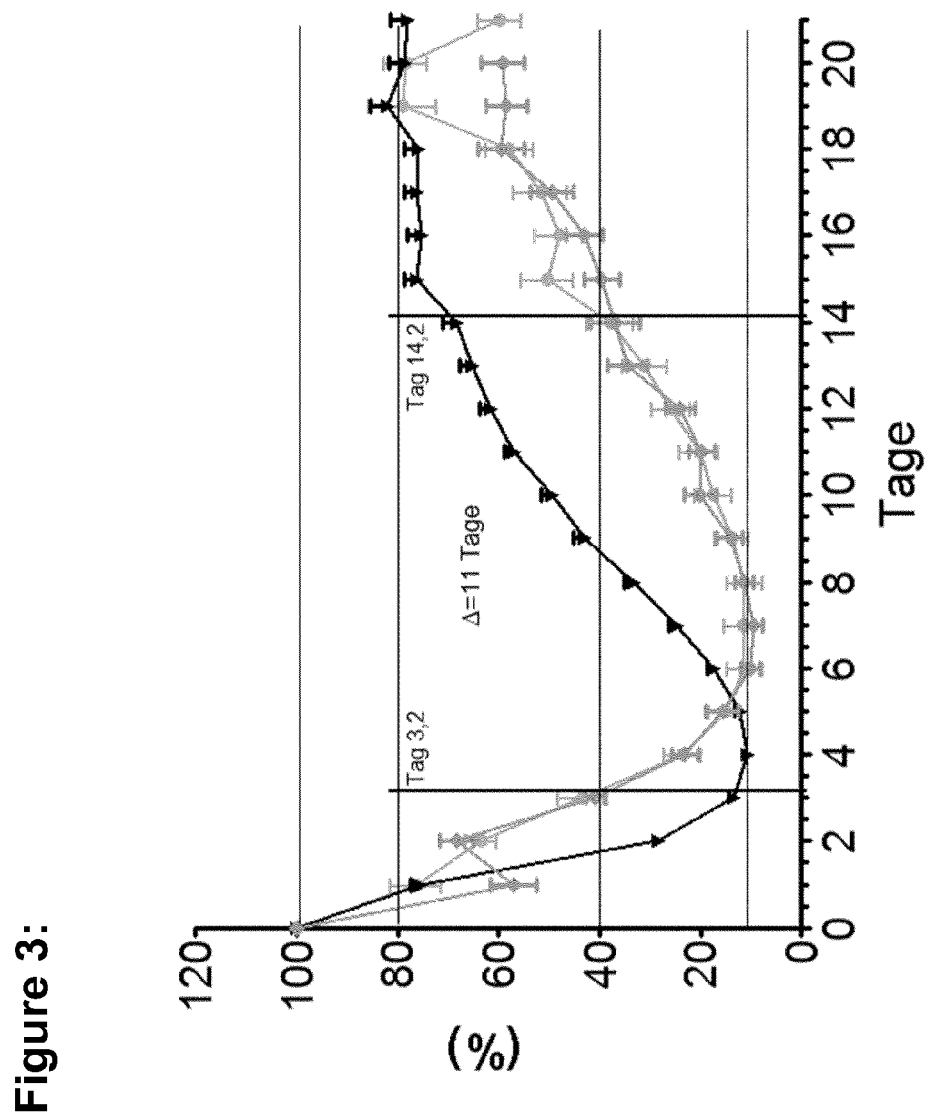

FIG. 3: Mouse running assay with PAS100-rBoNT/A-PAS100: ●, ◆: PAS100-rBoNT/A-PAS100 (two separate assays (MRA-159 and MRA-160), 9.0 pg of PAS100- rBoNT/A-PAS100 in each case); ▼: mean of standard (16 assays) from Xeomin® 81208 (0.6 U).

Figure 4:
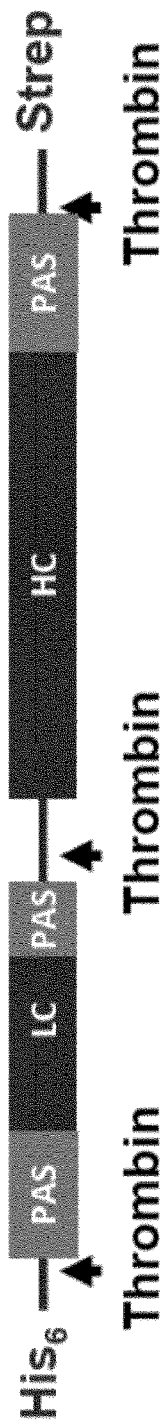
Figure 4:
Figure 4:
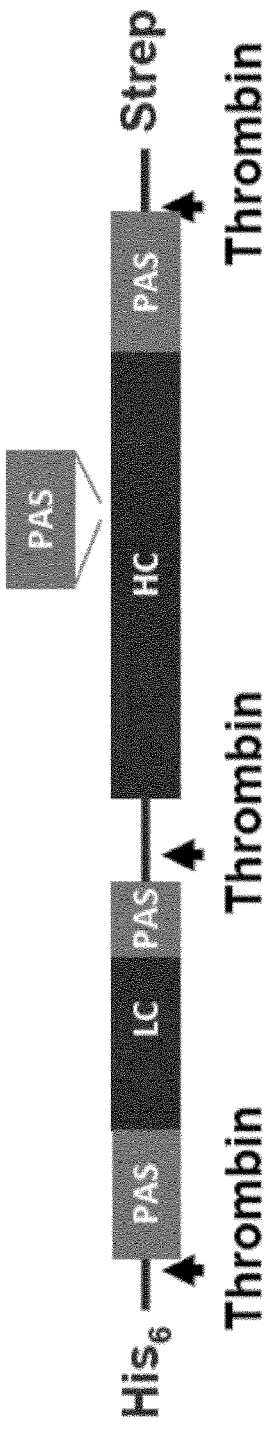

FIG. 4: Alternative constructs with three or four PAS domains: (A) PAS-BoNT-PAS with additional PAS sequence at the C-terminus of the light chain (alternative constructs possible with additional PAS sequence at the N-terminus of the heavy chain); (B) PAS-BoNT-PAS with additional PAS sequence between binding domain (C-terminus and translocation domain of the heavy chain; (C) PAS-BoNT-PAS with two additional PAS sequences at the C-terminus of the light chain and in an exposed loop of the heavy chain, respectively (alternative constructs possible with additional PAS sequence at the N-terminus of the heavy chain, and/or with additional PAS sequence in an exposed loop of the light chain).

DETAILED DESCRIPTION OF THE INVENTION

The present invention may be understood more readily by reference to the following detailed description of the invention and the examples included therein.

In one aspect, the present invention relates to a recombinant clostridial neurotoxin comprising at least two separate random coil domains.

In an alternative aspect, the present invention relates to recombinant clostridial neurotoxin comprising at least two domains having a polyproline II helix conformation.

In yet another aspect, the present invention relates to recombinant clostridial neurotoxin comprising at least two domains consisting of at least 50 amino acid residues selected from alanine (A), serine (S) and proline (P) residues.

In the context of the present invention, the term "clostridial neurotoxin" refers to a natural neurotoxin obtainable from bacteria of the class Clostridia, including *Clostridium tetani* and *Clostridium botulinum*, or to a neurotoxin obtainable from alternative sources, including from recombinant technologies or from genetic or chemical modification. Particularly, the clostridial neurotoxins have endopeptidase activity.

Clostridial neurotoxins are produced as single-chain precursors that are proteolytically cleaved by an unknown clostridial endoprotease within the loop region to obtain the biologically active disulfide-linked di-chain form of the neurotoxin, which comprises two chain elements, a functionally active light chain and a functionally active heavy chain, where one end of the light chain is linked to one end of the heavy chain not via a peptide bond, but via a disulfide bond.

In the context of the present invention, the term "clostridial neurotoxin light chain" refers to that part of a clostridial neurotoxin that comprises an endopeptidase activity responsible for cleaving one or more proteins that is/are part of the so-called SNARE-complex involved in the process resulting in the release of neurotransmitter into the synaptic cleft: In naturally occurring clostridial neurotoxins, the light chain has a molecular weight of approx. 50 kDa.

In the context of the present invention, the term "clostridial neurotoxin heavy chain" refers to that part of a clostridial neurotoxin that is responsible for entry of the neurotoxin into the neuronal cell: In naturally occurring clostridial neurotoxins, the heavy chain has a molecular weight of approx. 100 kDa.

In the context of the present invention, the term "functionally active clostridial neurotoxin chain" refers to a recombinant clostridial neurotoxin chain able to perform the biological functions of a naturally occurring *Clostridium botulinum* neurotoxin chain to at least about 50%, particularly to at least about 60%, to at least about 70%, to at least about 80%, and most particularly to at least about 90%, where the biological functions of clostridial neurotoxin chains include, but are not limited to, binding of the heavy chain to the neuronal cell, entry of the neurotoxin into a neuronal cell, release of the light chain from the di-chain neurotoxin, and endopeptidase activity of the light chain. Methods for determining a neurotoxic activity can be found, for example, in WO 95/32738, which describes the reconstitution of separately obtained light and heavy chains of tetanus toxin and botulinum toxin.

In the context of the present invention, the term "about" or "approximately" means within 20%, alternatively within 10%, including within 5% of a given value or range. Alternatively, especially in biological systems, the term "about" means within about a log (i.e. an order of magnitude), including within a factor of two of a given value.

In the context of the present invention, the term "recombinant clostridial neurotoxin" refers to a composition comprising a clostridial neurotoxin that is obtained by expression of the neurotoxin in a heterologous cell such as *E. coli*, and including, but not limited to, the raw material obtained from a fermentation process (supernatant, composition after cell lysis), a fraction comprising a clostridial neurotoxin obtained from separating the ingredients of such a raw material in a purification process, an isolated and essentially pure protein, and a formulation for pharmaceutical and/or aesthetic use comprising a clostridial neurotoxin and additionally pharmaceutically acceptable solvents and/or excipients.

In the context of the present invention, the term "recombinant clostridial neurotoxin" further refers to a clostridial neurotoxin based on a parental clostridial neurotoxin additionally comprising a heterologous domain, i.e. a random coil domain, or a domain having a polyproline II helix conformation, that is not naturally occurring in said parental clostridial neurotoxin, in particular a synthetic random coil domain, a synthetic domain having a polyproline II helix conformation, a random coil domain, or a domain having a polyproline II helix conformation, from a species other than *Clostridium botulinum*, in particular a random coil domain, or a domain having a polyproline II helix conformation, from a human protein.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components, or groups thereof. The term "comprising" thus includes the more restrictive terms "consisting of" and "consisting essentially of".

In the context of the present invention, the term "random coil domain" refers to a protein segment, which is essentially lacking a secondary structure. Random coil domains can be detected using a variety of methods, including spectroscopic methods such as circular dichroism or nuclear magnetic resonance (NMR) methods, including multidimensional NMR experiments, or crystallographic structure determinations.

In the context of the present invention, the term "domain having a polyproline II helix conformation" refers to a protein segment, which occurs in approx. 7% (8,000 out of 110,000) of all protein structures in the protein database PDB, and which is characterized by the following features:

(i) an extended left-handed helix; (ii) 3.1 Å per residue and 3 residues per turn (1.5 Å and 4 resdiues/turn in α-helix; 6 Å in β-sheet; 7.2 Å fully elongated); and (iii) a 3-fold rotational symmetry with shape of triangular prism. The polyproline II helix conformation is often found as short stretches helping conformational transition, such as in β-PPII, β-PPII or PPII-α. Domains having a polyproline II helix conformation can be detected using a variety of methods, including spectroscopic methods such as circular dichroism or nuclear magnetic resonance (NMR) methods, including multidimensional NMR experiments, or crystallographic structure determinations. In particular, in a Ramachandran Plot, polyproline II helix conformation is characterized by a psi angle of backbone close to that of anti-parallel-beta strands, and a phi angle that is close to alpha-helices (see Adzhubei et al., J. Mol. Biol. 425 (2013) 2100-32).

In particular embodiments, said random coil domain comprises an amino acid sequence consisting of at least 50 amino acid residues forming random coil conformation, particularly between 50 and 3000 amino acid residues, more particularly between 60 and 500 amino acid residues, more particularly between 70 and 260 amino acid residues, more particularly between 80 and 240 amino acid residues, more particularly between 90 and 220 amino acid residues, particularly 100 amino acid residues, 150 amino acid residues, or 200 amino acid residues.

In particular embodiments, said domain having a polyproline II helix conformation comprises an amino acid sequence consisting of at least 50 amino acid residues, particularly between 50 and 3000 amino acid residues, more particularly between 60 and 500 amino acid residues, more particularly between 70 and 260 amino acid residues, more particularly between 80 and 240 amino acid residues, more particularly between 90 and 220 amino acid residues, particularly 100 amino acid residues, 150 amino acid residues, or 200 amino acid residues.

In particular embodiments, said domain consists of alanine (A), serine (S) and proline (P) residues. These so-called "PAS" sequences (see, for example, Schlapschy et al., Protein Engineering, Design and Selection 26 (2013) 489-501; EP 2 369 005; WO 2011/144756) have been developed in order to extend the plasma half-life of pharmaceutically active proteins. It has been argued that the genetic fusion with such conformationally disordered polypeptide sequences provides a simple way to attach a solvated random chain with large hydrodynamic volume to the fusion partner, for example a protein of biopharmaceutical interest, so that the size of the resulting fusion protein is significantly increased, and that by these means the typically rapid clearance of the biologically active component via kidney filtration is retarded by one to two orders of magnitude. However, it is assumed that at least in part, such PAS sequences may alternatively form domains having a polyproline II helix conformation as well.

While it could be demonstrated that the fusion of a PAS-based domain to the N-terminus of a Botulinum neurotoxin light chain resulted in an extension of the duration of effect, as shown in WO 2015/132004, it was subsequently found that a fusion of such a PAS-based domain to the C-terminus of the heavy chain of a Botulinum neurotoxin did not exert any effect on the duration of effect, i.e. a Botulinum neurotoxin with mono-PASylation at the heavy chain C-terminus did not differ from the wildtype (see Comparative Examples 3 and 4). Therefore a markedly changed duration of effect could not be expected for a bis-PASylated Botulinum neurotoxin. However, the bis-PASylated neurotoxin exhibited a much longer duration than the mono-PASylated protein (see Examples 1 and 2). Thus, attachment of at least two random coil domains, or domains having a polyproline II helix conformation, such as at least two PAS-based domains, is able to extend the duration of effect of a protein that is active intracellularly even longer than the attachment of just a single such domain, as shown in WO 2015/132004.

In particular embodiments, at least one of said domains comprises a plurality of amino acid repeats, wherein said repeat consist of Ala, Ser, and Pro residues and wherein no more than six consecutive amino acid residues are identical. In particular embodiments, each of said domains comprises a plurality of amino acid repeats, wherein said repeat consist of Ala, Ser, and Pro residues and wherein no more than six consecutive amino acid residues are identical.

In particular embodiments, the proline residues comprised in at least one of said domains constitute more than 4% and less than 40% of the amino acids of said domain. In particular embodiments, the proline residues comprised in each of said domain constitute more than 4% and less than 40% of the amino acids of said domain.

In particular embodiments, at least one of said domains comprises at least one amino acid sequence selected from the group consisting of: ASPAAPAPASPAAPAPSAPA (SEQ ID NO: 1); AAPASPAPAAPSAPAPAAPS (SEQ ID NO: 2); APSSPSPSAPSSPSPASPSS (SEQ ID NO: 3), SAPSSPSPSAPSSPSPASPS (SEQ ID NO: 4), SSPSAPSPSSPASPSPSSPA (SEQ ID NO: 5), AASPAAPSAPPAAASPAAPSAPPA (SEQ ID NO: 6) and ASAAAPAAASAAASAPSAAA (SEQ ID NO: 7) or circular permuted versions or (a) multimer(s) of these sequences as a whole or parts of these sequences, particularly (ASPAAPAPASPAAPAPSAPA)$_n$, with n being (i) an integer selected from 3 to 25 (SEQ ID NO: 10), more particularly from 4 to 8 (SEQ ID NO: 11), more particularly from 5 to 10 (SEQ ID NO: 12), in particular wherein n is 5 (SEQ ID NO: 13) or 10 (SEQ ID NO: 14); or (ii) an integer selected from 5 to 150 (SEQ ID NO: 15), more particularly from 6 to 20 (SEQ ID NO: 16), more particularly from 7 to 13 (SEQ ID NO: 17), more particularly from 8 to 12 (SEQ ID NO: 18), more particularly from 9 to 11 (SEQ ID NO: 19), in particular wherein n is 10 (SEQ ID NO: 14). In particular embodiments, each of said domains comprises at least one amino acid sequence selected from the group consisting of: ASPAAPAPASPAAPAPSAPA (SEQ ID NO: 1); AAPASPAPAAPSAPAPAAPS (SEQ ID NO: 2); APSSPSPSAPSSPSPASPSS (SEQ ID NO: 3), SAPSSPSPSAPSSPSPASPS (SEQ ID NO: 4), SSPSAPSPSSPASPSPSSPA (SEQ ID NO: 5), AASPAAPSAPPAAASPAAPSAPPA (SEQ ID NO: 6) and ASAAAPAAASAAASAPSAAA (SEQ ID NO: 7) or circular permuted versions or (a) multimer(s) of these sequences as a whole or parts of these sequences, particularly (ASPAAPAPASPAAPAPSAPA)$_n$, with n being (i) an integer selected from 3 to 25 (SEQ ID NO: 10), more particularly from 4 to 8 (SEQ ID NO: 11), more particularly from 5 to 10 (SEQ ID NO: 12), in particular wherein n is 5 (SEQ ID NO: 13) or 10 (SEQ ID NO: 14); or (ii) an integer selected from 5 to 150 (SEQ ID NO: 15), more particularly from 6 to 20 (SEQ ID NO: 16), more particularly from 7 to 13 (SEQ ID NO: 17), more particularly from 8 to 12 (SEQ ID NO: 18), more particularly from 9 to 11 (SEQ ID NO: 19), in particular wherein n is 10 (SEQ ID NO: 14).

In particular embodiments, said at least two domains are inserted at at least two separate positions selected from (i) the N-terminus of the light chain of said recombinant clostridial neurotoxin; (ii) the C-terminus of the light chain of said recombinant clostridial neurotoxin; (iii) the N-terminus of the heavy chain of said recombinant clostridial neurotoxin; and (iv) the C-terminus of the heavy chain of said recombinant clostridial neurotoxin, particularly wherein a first such domain is inserted at the N-terminus of the light chain of said recombinant clostridial neurotoxin, and a second such domain is inserted at the C-terminus of the heavy chain of said recombinant clostridial neurotoxin.

In particular embodiments, said three domains are inserted at three separate positions selected from (i) the N-terminus of the light chain of said recombinant clostridial neurotoxin; (ii) the C-terminus of the light chain of said recombinant clostridial neurotoxin; (iii) the N-terminus of the heavy chain of said recombinant clostridial neurotoxin; (iv) the C-terminus of the heavy chain of said recombinant clostridial neurotoxin, (v) between the C-terminal binding domain of the heavy chain and the translocatation domain of the heavy chain, and (vi) in an exposed loop of the heavy chain or light chain.

In particular embodiments, one of said domains is inserted in the toxin's light chain in a position between amino acid residue 123 and P31 (residue numbering of 3BTA.pdb) (loop 20/30), in a position between amino acid residue D48 and T79 (loop 60/70), in a position between amino acid residue G113 and N132 (loop 120/130), in a position between amino acid residue P155 and F162 (loop 160), in a position between amino acid residue S166 and T182 (loop 170/180), in a position between amino acid residue E196 and K211 (loop 200), in a position between amino acid residue Y232 and S258 (loop 250), in a position between amino acid residue G266 and D274 (loop 270), in a position between amino acid residue K298 and S308 (loop 300), in a position between amino acid residue D325 and K329 (loop 320), in a position between amino acid residue K358 and V372 (loop 360/370), in a position between amino acid residue 1376 and F401 (loop 380/390).

In particular embodiments, one of said domains is inserted in the translocation domain (HN) of the heavy chain of the toxin in a position between amino acid residue S466 and G477 (residue numbering of 3BTA.pdb) (loop 470), in a position between amino acid residue T481 and S494 (loop 480), in a position between amino acid residue T504 and K540 (toxin's belt), in a position between amino acid residue A555 and V571 (loop 560), in a position between amino acid residue L576 and S586 (loop 580), in a position between amino acid residue N594 and F602 (loop 600), in a position between amino acid residue T617 and 1633 (loop 620), in a position between amino acid residue G637 and F651 (loop 640/650), in a position between amino acid residue L664 and T677 (loop 670), in a position between amino acid residue V681 and N686 (loop 680), in a position between amino acid residue N751-1765 (loop 760), in a position between amino acid residue D824 and 1830 (loop 820), and in a position between amino acid residue L844 and N858 (loop 850).

In particular embodiments, one of said domains is inserted in the N-terminal domain of the binding domain (HC$_N$) of the heavy chain of the toxin in a position between amino acid residue G900 and N911 (residue numbering of 3BTA.pdb) (loop 900), in a position between amino acid residue N917 and K922 (loop 920), in a position between amino acid residue K928 and N934 (loop 930), in a position between amino acid residue 1948 and N959 (loop 950), in a position between amino acid residue C966 and W973 (loop 970), in a position between amino acid residue D988 and 1992 (loop 990), in a position between amino acid residue Y1000 and R1012 (loop 1000/1010), in a position between amino acid residue 11040 and N1050 (loop 1040), and in a position between amino acid residue G1058 and R1064 (loop 1060).

In particular embodiments, one of said domains is inserted in the C-terminal domain of the binding domain (HC$_C$) of the heavy chain of the toxin in a position between amino acid residue 11090 and P1109 (residue numbering of 3BTA.pdb) (loop 1100), in a position between amino acid residue L1113 and K1120 (loop 1120), in a position between amino acid residue N1125 and Y1132 (loop 1130), in a position between amino acid residue G1137 and T1157 (loop 1140/1150), in a position between amino acid residue K1163 and D1177 (loop 1170), in a position between amino acid residue T1194 and L1205 (loop 1200), in a position between amino acid residue E1209 and V1219 (loop 1210), in a position between amino acid residue K1223 and K1235 (loop 1230), in a position between amino acid residue Q1239 and 11246 (loop 1240), in a position between amino acid residue Q1253 and A1282 (loop 1250), and in a position between amino acid residue 11270 and E1282 (loop 1280).

In particular embodiments, a first of said domains is inserted at the N-terminus of the light chain of said recombinant clostridial neurotoxin, a second of said domains is inserted at the C-terminus of the heavy chain of said recombinant clostridial neurotoxin, and a third of said domains is inserted at the C-terminus of the light chain or the N-terminus of the heavy chain, particularly at the C-terminus of the light chain.

In particular other embodiments, a first of said domains is inserted at the N-terminus of the light chain of said recombinant clostridial neurotoxin, a second of said domains is inserted at the C-terminus of the heavy chain of said recombinant clostridial neurotoxin, and a third of said domains is inserted between the C-terminal binding domain of the heavy chain and the translocation domain of the heavy chain.

In particular other embodiments, a first of said domains is inserted at the N-terminus of the light chain of said recombinant clostridial neurotoxin, a second of said domains is inserted at the C-terminus of the heavy chain of said recombinant clostridial neurotoxin, and a third of said domains is inserted in an exposed loop of the heavy chain.

In particular embodiments, four of said domains are inserted at the following four positions: (i) the N-terminus of the light chain of said recombinant clostridial neurotoxin; (ii) the C-terminus of the light chain of said recombinant clostridial neurotoxin; (iii) the N-terminus of the heavy chain of said recombinant clostridial neurotoxin; and (iv) the C-terminus of the heavy chain of said recombinant clostridial neurotoxin.

In particular embodiments, the sequence of said clostridial neurotoxin is selected from the sequence of (i) a *Clostridium botulinum* neurotoxin serotype A, B, C, D, E, F, G, and H, particularly *Clostridium botulinum* neurotoxin serotype A, C and E, particularly *Clostridium botulinum* neurotoxin serotype A, or (ii) from the sequence of a functional variant of a *Clostridium botulinum* neurotoxin of (i), or (iii) from the sequence of a chimeric *Clostridium botulinum* neurotoxin, wherein the clostridial neurotoxin light chain and heavy chain are from different parental clostridial neurotoxin serotypes.

In the context of the present invention, the term "*Clostridium botulinum* neurotoxin serotype A, B, C, D, E, F, G, and H" refers to neurotoxins found in and obtainable from *Clostridium botulinum*. Currently, seven serologically distinct types, designated serotypes A, B, C, D, E, F, G, and H are known, including certain subtypes (e.g. A1, A2, A3, A4 etc.).

In particular embodiments the clostridial neurotoxin is selected from a *Clostridium botulinum* neurotoxin serotype A, C and E, in particular from *Clostridium botulinum* neurotoxin serotype A, or from a functional variant of any such *Clostridium botulinum* neurotoxin.

In particular embodiments, said recombinant clostridial neurotoxin has a light chain and a heavy chain comprised in the amino acid sequence as found in SEQ ID NO: 8 (see Table 1).

In the context of the present invention, the term "functional variant of a clostridial neurotoxin" refers to a neurotoxin that differs in the amino acid sequence and/or the nucleic acid sequence encoding the amino acid sequence from a clostridial neurotoxin, but is still functionally active. In the context of the present invention, the term "functionally active" refers to the property of a recombinant clostridial neurotoxin to exhibit a biological activity of at least about 50%, particularly to at least about 60%, at least about 70%, at least about 80%, and most particularly at least about 90% of the biological activity of a naturally occurring parental clostridial neurotoxin, i.e. a parental clostridial neurotoxin without a random coil domain or without a domain having a polyproline II helix conformation, where the biological functions include, but are not limited to, binding to the neurotoxin receptor, entry of the neurotoxin into a neuronal cell, translocation of the light chain into the cytosol, and endopeptidase activity of the light chain, and thus inhibition of neurotransmitter release from the affected nerve cell. For the sake of clarity, when comparing the functional activity of a given variant with a parental clostridial neurotoxin in accordance with the present definition, the activity of non-PASylated neurotoxins is compared.

On the protein level, a functional variant will maintain key features of the corresponding clostridial neurotoxin, such as key residues for the endopeptidase activity in the light chain, or key residues for the attachment to the neurotoxin receptors or for translocation through the endosomal membrane in the heavy chain, but may contain one or more mutations comprising a deletion of one or more amino acids of the corresponding clostridial neurotoxin, an addition of one or more amino acids of the corresponding clostridial neurotoxin, and/or a substitution of one or more amino acids of the corresponding clostridial neurotoxin. Particularly, said deleted, added and/or substituted amino acids are consecutive amino acids. According to the teaching of the present invention, any number of amino acids may be added, deleted, and/or substituted, as long as the functional variant remains biologically active. For example, 1, 2, 3, 4, 5, up to 10, up to 15, up to 25, up to 50, up to 100, up to 200, up to 400, up to 500 amino acids or even more amino acids may be added, deleted, and/or substituted. Accordingly, a functional variant of the neurotoxin may be a biologically active fragment of a naturally occurring neurotoxin. This neurotoxin fragment may contain an N-terminal, C-terminal, and/or one or more internal deletion(s).

In another embodiment, the functional variant of a clostridial neurotoxin additionally comprises a signal peptide. Usually, said signal peptide will be located at the N-terminus of the neurotoxin. Many such signal peptides are known in the art and are comprised by the present invention. In particular, the signal peptide results in transport of the neurotoxin across a biological membrane, such as the membrane of the endoplasmic reticulum, the Golgi membrane or the plasma membrane of a eukaryotic or prokaryotic cell. It has been found that signal peptides, when attached to the neurotoxin, will mediate secretion of the neurotoxin into the supernatant of the cells. In certain embodiments, the signal peptide will be cleaved off in the course of, or subsequent to, secretion, so that the secreted protein lacks the N-terminal signal peptide, is composed of separate light and heavy chains, which are covalently linked by disulfide bridges, and is proteolytically active.

In particular embodiments, the functional variant has in its *clostridium* neurotoxin part a sequence identity of at least about 40%, at least about 50%, at least about 60%, at least about 70% or most particularly at least about 80%, and a sequence homology of at least about 60%, at least about 70%, at least about 80%, at least about 90%, or most particularly at least about 95% to the corresponding part in the parental clostridial neurotoxin. Methods and algorithms for determining sequence identity and/or homology, including the comparison of variants having deletions, additions, and/or substitutions relative to a parental sequence, are well known to the practitioner of ordinary skill in the art. On the DNA level, the nucleic acid sequences encoding the functional homologue and the parental clostridial neurotoxin may differ to a larger extent due to the degeneracy of the genetic code. It is known that the usage of codons is different between prokaryotic and eukaryotic organisms. Thus, when expressing a prokaryotic protein such as a clostridial neurotoxin, in a eukaryotic expression system, it may be necessary, or at least helpful, to adapt the nucleic acid sequence to the codon usage of the expression host cell, meaning that sequence identity or homology may be rather low on the nucleic acid level.

In the context of the present invention, the term "variant" refers to a neurotoxin that is a chemically, enzymatically, or genetically modified derivative of a corresponding clostridial neurotoxin, including chemically or genetically modified neurotoxin from *C. botulinum*, particularly of *C. botulinum* neurotoxin serotype A, C or E. A chemically modified derivative may be one that is modified by pyruvation, phosphorylation, sulfatation, lipidation, pegylation, glycosylation and/or the chemical addition of an amino acid or a polypeptide comprising between 2 and about 100 amino acids, including modification occurring in the eukaryotic host cell used for expressing the derivative. An enzymatically modified derivative is one that is modified by the activity of enzymes, such as endo- or exoproteolytic enzymes, including modification by enzymes of the eukaryotic host cell used for expressing the derivative. As pointed out above, a genetically modified derivative is one that has been modified by deletion or substitution of one or more amino acids contained in, or by addition of one or more amino acids (including polypeptides comprising between 2 and about 100 amino acids) to, the amino acid sequence of said clostridial neurotoxin. Methods for designing and constructing such chemically or genetically modified derivatives and for testing of such variants for functionality are well known to anyone of ordinary skill in the art.

In particular embodiments, said recombinant clostridial neurotoxin shows increased duration of effect relative to an identical clostridial neurotoxin without any of said domains. In particular embodiment, said recombinant clostridial neurotoxin shows increased duration of effect relative to an identical clostridial neurotoxin with only one of said domains.

In the context of the present invention, the term "increased duration of effect" or "increased duration of action" refers to a longer lasting denervation mediated by a clostridial neurotoxin of the present invention. For example, as disclosed herein, administration of a disulfide-linked di-chain clostridial neurotoxin comprising said domains results in localized paralysis for a longer period of time relative to administration of an identical disulfide-linked di-chain clostridial neurotoxin without such domains.

In the context of the present invention, the term "increased duration of effect/action" is defined as a more than about 20%, particularly more than about 50%, more particularly more than about 90% increased duration of effect of the recombinant neurotoxin of the present invention relative to the identical neurotoxin without said domains.

In the context of the present invention the term "denervation" refers to denervation resulting from administration of a chemodenervating agent, for example a neurotoxin.

In the context of the present invention, the term "localized denervation" or "localized paralysis" refers to denervation of a particular anatomical region, usually a muscle or a group of anatomically and/or physiologically related muscles, which results from administration of a chemodenervating agent, for example a neurotoxin, to the particular anatomical region.

Without wishing to be bound by theory, the recombinant clostridial neurotoxins of the present invention might show increased biological half-life, reduced degradation rates, decreased diffusion rates, increased uptake by neuronal cells, and/or modified intracellular translocation rates, in each case relative to an identical parental clostridial neurotoxin without said domains.

In particular embodiments, the increased duration of effect is due to an increased biological half-life.

In the context of the present invention, the term "biological half-life" specifies the lifespan of a protein, for example of a clostridial neurotoxin, in vivo. In the context of the present invention, the term "biological half-life" refers to the period of time, by which half of a protein pool is degraded in vivo. For example it refers to the period of time, by which half of the amount of clostridial neurotoxin of one administered dosage is degraded.

In the context of the present invention, the term "increased biological half-life" is defined as a more than about 20%, particularly more than about 50%, more particularly more than about 90% increased biological half-life of the recombinant neurotoxin of the present invention relative to the identical neurotoxin without said domains.

In the context of the present invention, the term "reduced degradation rate" means that said domains (PAS sequences) protect the light chain and/or the heavy chain against degradation processes, such as, for example, the attack of proteases or modifying enzymes like E3 ligases. Particularly in the case of one or more of said domains (PAS sequences) connected to the light chain, the light chain is protected against such degradation processes in the cytosol of the neuron. Because of this protection the half-life of the light chain in the neuron is extended resulting in a longer duration of the therapeutic effect.

Without wishing to be bound by theory it appears to be possible the increased duration of effect is due to a factor selected from reduced diffusion, increased uptake by neurons, modified uptake by neurons, modified interaction of the recombinant neurotoxin with the extracellular matrix and/or modified receptor binding, particularly in cases where one or more of said domains (PAS sequences) are connected to the heavy chain.

In particular embodiments, the recombinant clostridial neurotoxin is for the use in the treatment of a disease requiring improved chemodenervation, wherein the recombinant clostridial neurotoxin causes longer lasting denervation relative to an identical clostridial neurotoxin without, or with just a single of, said domains.

In particular other embodiments, the recombinant clostridial neurotoxin is of serotype E and is for use in the treatment of (a) patients showing an immune reaction against BoNT/A, or (b) headache or epilepsy.

In another aspect, the present invention relates to a pharmaceutical composition comprising the recombinant clostridial neurotoxin of the present invention.

In particular embodiments, the recombinant clostridial neurotoxin of the present invention or the pharmaceutical composition of the present invention is for use in the treatment of a disease or condition taken from the list of: cervical dystonia (spasmodic torticollis), blepharospasm, severe primary axillary hyperhidrosis, achalasia, lower back pain, benign prostate hypertrophy, chronic focal painful neuropathies, migraine and other headache disorders.

Additional indications where treatment with botulinum neurotoxins is currently under investigation and where the pharmaceutical composition of the present invention may be used, include pediatric incontinence, incontinence due to overactive bladder, and incontinence due to neurogenic bladder, anal fissure, spastic disorders associated with injury or disease of the central nervous system including trauma, stroke, multiple sclerosis, Parkinson's disease, or cerebral palsy, focal dystonias affecting the limbs, face, jaw or vocal cords, temporomandibular joint (TMJ) pain disorders, diabetic neuropathy, wound healing, excessive salivation, vocal cord dysfunction, reduction of the Masseter muscle for decreasing the size of the lower jaw, treatment and prevention of chronic headache and chronic musculoskeletal pain, treatment of snoring noise, assistance in weight loss by increasing the gastric emptying time.

Most recently, clostridial neurotoxins have been evaluated for the treatment of other new indications, for example painful keloid, diabetic neuropathic pain, refractory knee pain, trigeminal neuralgia trigger-zone application to control pain, scarring after cleft-lip surgery, cancer and depression.

Thus, in another aspect the present invention relates to a method of treating a patient suffering from a disease associated with increased or aberrant muscle activity, including a disease or disorder mentioned above in [0082] to [0084], comprising the step of administering a composition comprising a recombinant clostridial neurotoxin according to the present invention to said patient.

In yet another aspect, the present invention relates to the use of the composition of the present invention for a cosmetic treatment.

Thus, in another aspect, the present invention relates to a method of cosmetically treating a patient, comprising the step of administering a composition comprising a recombinant clostridial neurotoxin according to the present invention to a patient desiring such cosmetic treatment.

In the context of the present invention, the terms "cosmetic treatment" or "cosmetically treating" relate to uses in cosmetic or aesthetic applications, such as the treatment of wrinkles, crow's feet, frown lines etc.

In another aspect, the present invention relates to a method for the generation of the recombinant clostridial neurotoxin of the present invention, comprising the step of obtaining a recombinant nucleic acid sequence encoding a recombinant single-chain precursor clostridial neurotoxin by the insertion of one or more nucleic acid sequences each encoding one of said domains at at least two positions into a nucleic acid sequence encoding a parental clostridial neurotoxin.

In the context of the present invention, the term "recombinant nucleic acid sequence" refers to a nucleic acid, which has been generated by joining genetic material from two different sources.

In the context of the present invention, the term "single-chain precursor clostridial neurotoxin" refers to a single-chain precursor for a disulfide-linked di-chain clostridial neurotoxin, comprising a functionally active clostridial neurotoxin light chain, a functionally active neurotoxin heavy chain, and a loop region linking the C-terminus of the light chain with the N-terminus of the heavy chain.

In the context of the present invention, the term "recombinant single-chain precursor clostridial neurotoxin" refers to a single-chain precursor clostridial neurotoxin comprising at least two heterologous random coil domains or domains having a polyproline II helix conformation, i.e. domains independently selected from a species other than *Clostridium botulinum*.

In particular embodiments, the recombinant single-chain precursor clostridial neurotoxin comprises a protease cleavage site in said loop region.

Single-chain precursor clostridial neurotoxins have to be proteolytically cleaved to obtain the final biologically active clostridial neurotoxins. Proteolytic cleavage may either occur during heterologous expression by host cell enzymes, or by adding proteolytic enzymes to the raw protein material isolated after heterologous expression. Naturally occurring clostridial neurotoxins usually contain one or more cleavage signals for proteases which post-translationally cleave the single-chain precursor molecule, so that the final di- or multimeric complex can form. At present, clostridial neurotoxins are still predominantly produced by fermentation processes using appropriate *Clostridium* strains. During the fermentation process, the single-chain precursors are proteolytically cleaved by an unknown clostridial protease to obtain the biologically active di-chain clostridial neurotoxin. In cases, where the single-chain precursor molecule is the precursor of a protease, autocatalytic cleavage may occur. Alternatively, the protease can be a separate non-clostridial enzyme expressed in the same cell. WO 2006/076902 describes the proteolytic cleavage of a recombinant clostridial neurotoxin single-chain precursor at a heterologous recognition and cleavage site by incubation of the *E. coli* host cell lysate. The proteolytic cleavage is carried out by an unknown *E. coli* protease. In certain applications of recombinant expression, modified protease cleavage sites have been introduced recombinantly into the interchain region between the light and heavy chain of clostridial toxins, e.g. protease cleavage sites for human thrombin or non-human proteases (see WO 01/14570).

In particular embodiments, the protease cleavage site is a site that is cleaved by a protease selected from the list of: a protease selected from the list of: thrombin, trypsin, enterokinase, factor Xa, plant papain, insect papain, crustacean papain, enterokinase, human rhinovirus 3C protease, human enterovirus 3C protease, tobacco etch virus protease, Tobacco Vein Mottling Virus, subtilisin and caspase 3.

In a particular embodiment, the recombinant single-chain precursor clostridial neurotoxin further comprises a binding tag, particularly selected from the group comprising: glutathione-S-transferase (GST), maltose binding protein (MBP), a His-tag, a Strep-tag®, or a FLAG-tag.

In the context of the present invention, the term "parental clostridial neurotoxin" refers to an initial clostridial neurotoxin without any heterologous random coil domain, or domain having a polyproline II helix conformation, selected from a natural clostridial neurotoxin, a functional variant of a natural clostridial neurotoxin or a chimeric clostridial neurotoxin, wherein the clostridial neurotoxin light chain and heavy chain are from different clostridial neurotoxin serotypes.

In particular embodiments, the method for the generation of the recombinant clostridial neurotoxin of the present invention further comprises the step of heterologously expressing said recombinant nucleic acid sequence in a host cell, particularly in a bacterial host cell, more particularly in an *E. coli* host cell.

In certain embodiments, the *E. coli* cells are selected from *E. coli* XL1-Blue, Nova Blue, TOP10, XL10-Gold, BL21, and K12.

In particular embodiments, the method for the generation of the recombinant clostridial neurotoxin of the present invention additionally comprises at least one of the steps of (i) generating a disulfide-linked di-chain recombinant clostridial neurotoxin comprising at least two random coil domains, or at least two domains having a polyproline II helix conformation, by causing or allowing contacting of said recombinant single-chain precursor clostridial neurotoxin with an endoprotease and (ii) purification of said recombinant single-chain precursor clostridial neurotoxin or said disulfide-linked di-chain recombinant clostridial neurotoxin by chromatography.

In particular embodiments, the recombinant single-chain precursor clostridial neurotoxin, or the recombinant disulfide-linked di-chain clostridial neurotoxin, is purified after expression, or in the case of the recombinant disulfide-linked di-chain clostridial neurotoxin, after the cleavage reaction. In particular such embodiments, the protein is purified by chromatography, particularly by immunoaffinity chromatography, or by chromatography on an ion exchange matrix, a hydrophobic interaction matrix, or a multimodal chromatography matrix, particularly a strong ion exchange matrix, more particularly a strong cation exchange matrix.

In the context of the present invention, the term "causing . . . contacting of said recombinant single-chain precursor clostridial neurotoxin . . . with an endoprotease" refers to an active and/or direct step of bringing said neurotoxin and said endoprotease in contact, whereas the term "allowing contacting of a recombinant single-chain precursor clostridial neurotoxin . . . with an endoprotease" refers to an indirect step of establishing conditions in such a way that said neurotoxin and said endoprotease are getting in contact to each other.

In the context of the present invention, the term "endoprotease" refers to a protease that breaks peptide bonds of non-terminal amino acids (i.e. within the polypeptide chain). As they do not attack terminal amino acids, endoproteases cannot break down peptides into monomers.

In particular embodiments, cleavage of the recombinant single-chain precursor clostridial neurotoxin is near-complete.

In the context of the present invention, the term "near-complete" is defined as more than about 95% cleavage, particularly more than about 97.5%, more particularly more than about 99% as determined by SDS-PAGE and subsequent Western Blot or reversed phase chromatography.

In particular embodiments, cleavage of the recombinant single-chain precursor clostridial neurotoxin occurs at a heterologous cleavage signal located in the loop region of the recombinant precursor clostridial neurotoxin.

In particular embodiments, the cleavage reaction is performed with crude host cell lysates containing said single-chain precursor protein.

In other particular embodiments, the single-chain precursor protein is purified or partially purified, particularly by a first chromatographic enrichment step, prior to the cleavage reaction.

In the context of the present invention, the term "purified" relates to more than about 90% purity. In the context of the present invention, the term "partially purified" relates to purity of less than about 90% and an enrichment of more than about two fold.

In another aspect, the present invention relates to a recombinant single-chain clostridial neurotoxin, which is a precursor for the recombinant clostridial neurotoxin of the present invention Thus, in such aspect, the present invention relates to a recombinant single-chain precursor clostridial neurotoxin comprising at least two separate random coil domainsm, or at least two domains having a polyproline II helix conformation.

In particular embodiments, at least one of said domains comprises an amino acid sequence consisting of at least 50 amino acid residues, particularly between 50 and 3000 amino acid residues, more particularly between 60 and 500 amino acid residues, more particularly between 70 and 260 amino acid residues, more particularly between 80 and 240 amino acid residues, more particularly between 90 and 220 amino acid residues, particularly 100 amino acid residues, 150 amino acid residues, or 200 amino acid residues. In particular embodiments, each of said domains comprises an amino acid sequence consisting of at least 50 amino acid residues, particularly between 50 and 3000 amino acid residues, more particularly between 60 and 500 amino acid residues, more particularly between 70 and 260 amino acid residues, more particularly between 80 and 240 amino acid residues, more particularly between 90 and 220 amino acid residues, particularly 100 amino acid residues, 150 amino acid residues, or 200 amino acid residues.

In particular embodiments, at least one of said domains consists of alanine, serine and proline residues. In particular embodiments, each of said domains consists of alanine, serine and proline residues.

In particular embodiments, at least one of said domains comprises a plurality of amino acid repeats, wherein said repeat consist of Ala, Ser, and Pro residues and wherein no more than 6 consecutive amino acid residues are identical. In particular embodiments, each of said domains comprises a plurality of amino acid repeats, wherein said repeat consist of Ala, Ser, and Pro residues and wherein no more than 6 consecutive amino acid residues are identical.

In particular embodiments, in at least one of said domains the proline residues comprised in said domain constitute more than 4% and less than 40% of the amino acids of said domain. In particular embodiments, in each of said domains the proline residues comprised in said domain constitute more than 4% and less than 40% of the amino acids of said domain.

In particular embodiments, at least one of said domains comprises at least one amino acid sequence selected from the group consisting of: ASPAAPAPASPAAPAPSAPA (SEQ ID NO: 1); AAPASPAPAAPSAPAPAAPS (SEQ ID NO: 2); APSSPSPSAPSSPSPASPSS (SEQ ID NO: 3), SAPSSPSPSAPSSPSPASPS (SEQ ID NO: 4), SSPSAPSPSSPASPSPSSPA (SEQ ID NO: 5), AASPAAPSAPPAAASPAAPSAPPA (SEQ ID NO: 6) and ASAAAPAAASAAASAPSAAA (SEQ ID NO: 7) or circular permuted versions or (a) multimer(s) of these sequences as a whole or parts of these sequences, particularly (ASPAAPAPASPAAPAPSAPA)$_n$, with n being (i) an integer selected from 3 to 25 (SEQ ID NO: 10), more particularly from 4 to 8 (SEQ ID NO: 11), more particularly from 5 to 10 (SEQ ID NO: 12), in particular wherein n is 5 (SEQ ID NO: 13) or 10 (SEQ ID NO: 14); or (ii) an integer selected from 5 to 150 (SEQ ID NO: 15), more particularly from 6 to 20 (SEQ ID NO: 16), more particularly from 7 to 13 (SEQ ID NO: 17), more particularly from 8 to 12 (SEQ ID NO: 18), more particularly from 9 to 11 (SEQ ID NO: 19), in particular wherein n is 10 (SEQ ID NO: 14). In particular embodiments, each of said domains comprises at least one amino acid sequence selected from the group consisting of: ASPAAPAPASPAAPAPSAPA (SEQ ID NO: 1); AAPASPAPAAPSAPAPAAPS (SEQ ID NO: 2); APSSPSPSAPSSPSPASPSS (SEQ ID NO: 3), SAPSSPSPSAPSSPSPASPS (SEQ ID NO: 4), SSPSAPSPSSPASPSPSSPA (SEQ ID NO: 5), AASPAAPSAPPAAASPAAPSAPPA (SEQ ID NO: 6) and ASAAAPAAASAAASAPSAAA (SEQ ID NO: 7) or circular permuted versions or (a) multimer(s) of these sequences as a whole or parts of these sequences, particularly (ASPAAPAPASPAAPAPSAPA)$_n$, with n being (i) an integer selected from 3 to 25 (SEQ ID NO: 10), more particularly from 4 to 8 (SEQ ID NO: 11), more particularly from 5 to 10 (SEQ ID NO: 12), in particular wherein n is 5 (SEQ ID NO: 13) or 10 (SEQ ID NO: 14); or (ii) an integer selected from 5 to 150 (SEQ ID NO: 15), more particularly from 6 to 20 (SEQ ID NO: 16), more particularly from 7 to 13 (SEQ ID NO: 17), more particularly from 8 to 12 (SEQ ID NO: 18), more particularly from 9 to 11 (SEQ ID NO: 19), in particular wherein n is 10 (SEQ ID NO: 14).

In particular embodiments, said domain(s) is/are inserted at (i) the N-terminus of the light chain of said recombinant clostridial neurotoxin; (ii) the C-terminus of the light chain of said recombinant clostridial neurotoxin; (i) the N-terminus of the heavy chain of said recombinant clostridial neurotoxin; and/or (ii) the C-terminus of the heavy chain of said recombinant clostridial neurotoxin.

In particular embodiments, the sequence of said clostridial neurotoxin is selected from the sequence of (i) a *Clostridium botulinum* neurotoxin serotype A, B, C, D, E, F, G, and H, particularly *Clostridium botulinum* neurotoxin serotype A, C and E, more particularly *Clostridium botulinum* neurotoxin serotype A, or (ii) from the sequence of a functional variant of a *Clostridium botulinum* neurotoxin of (i), or (iii) from the sequence of a chimeric *Clostridium botulinum* neurotoxin, wherein the clostridial neurotoxin light chain and heavy chain are from different clostridial neurotoxin serotypes.

In particular embodiments, said recombinant single-chain clostridial neurotoxin has the amino acid sequence as found in SEQ ID NO: 8 (see Table 1).

In another aspect, the present invention relates to a nucleic acid sequence encoding the recombinant single-chain clostridial neurotoxin of the present invention, particularly a nucleic acid sequence as found SEQ ID NO: 9 (see Table 1).

In another aspect, the present invention relates to a method for obtaining the nucleic acid sequence of the present invention, comprising the step of inserting one or more nucleic acid sequences each encoding one of said domains at at least two positions into a nucleic acid sequence encoding a parental clostridial neurotoxin.

In another aspect, the present invention relates to a vector comprising the nucleic acid sequence of the present invention, or the nucleic acid sequence obtainable by the method of the present invention.

In another aspect, the present invention relates to a recombinant host cell comprising the nucleic acid sequence of the present invention, the nucleic acid sequence obtainable by the method of the present invention, or the vector of the present invention.

In certain embodiments, the recombinant host cells are selected from E. coli XL1-Blue, Nova Blue, TOP10, XL10-Gold, BL21, and K12.

In another aspect, the present invention relates to a method for producing the recombinant single-chain precursor clostridial neurotoxin of the present invention, comprising the step of expressing the nucleic acid sequence of the present invention, or the nucleic acid sequence obtainable by the method of the present invention, or the vector of the present invention in a recombinant host cell, or cultivating the recombinant host cell of the present invention under conditions that result in the expression of said nucleic acid sequence.

EXAMPLES

Example 1: Generation and Purification of a Bis-PASylated Botulinum Toxin Type A (PAS100-rBoNT/A-PAS100

The nucleic acid construct encoding a "PAS" module comprising 100 amino acid residues built from the amino acids proline, serine and alanine was synthetically produced. By using restriction enzymes NdeI and SwaI, the corresponding gene module was first inserted at the N-teminus of recombinant BoNT/A (rBoNT/A). In a second step, the PAS module was inserted at the C-terminus of the heavy chain by using restriction enzymes BglII and AatII (FIG. 1). The correct cloning was verified by sequencing.

Expression was performed in expression strain E. coli B121 using Riesenberg medium (Riesenberg D, Schulz V, Knorre W A, Pohl H D, Korz D, Sanders E A, Ross A, Deckwer W D: High cell density cultivation of Escherichia coli at controlled specific growth rate. J Biotechnol 1991, 20(1):17-27). Purification was done using a combination of affinity (HIS and STREP tag) and size exclusion chromatography, followed by activation using thrombin, which cleaved off the affinity tags as well. FIG. 2 summarizes the results of purification and activation.

Example 2: Duration of Effect of PAS100-rBoNT/A-PAS100 in a "Mouse Running Assay"

Equipotent dosages of PAS100-rBoNT/A-PAS100 or Xeomin® were injected into the M. gastrocnemius of eight mice each that had been trained in a treadmill. Using these dosages, only a sub-maximum paralysis was observed in order to exclude potential systemic effects as far as possible, which may have an impact on the duration of effect. The daily running distance in the treadmill was measured over 15 days. The paralysis caused by the toxins was plotted as percentage of the running distance on the day before the injection, which was set as 100%, against the time (see FIG. 3).

The injection of PAS100-rBoNT/A-PAS100 resulted in a maximum paralysis after 7 days, for the control group treated with Xeomin® maximum paralysis was observed after 4 days. During the recovery phase the running distance of the control group reached a value of 40% of the starting value 5 days after maximum paralysis was observed (day 9), whereas the group treated with PAS100-rBoNT/A-PAS100 reached that value 7 days after maximum paralysis (day 15). Thus, the duration of effective paralysis was significantly extended.

Comparative Example 3: Generation and Purification of a Botulinum Toxin Type A PASylated at the C-terminus of Heavy Chain (rBoNT/A-PAS100

The nucleic acid construct encoding a "PAS" module comprising 100 amino acid residues built from the amino acids proline, serine and alanine was synthetically produced. By using restriction enzymes AatII & BglIII, the corresponding gene module was inserted at the C-teminus of the heavy chain of recombinant BoNT/A (rBoNT/A). The correct cloning was verified by sequencing.

Expression was performed in expression strain E. coli B121 using Riesenberg medium (Riesenberg D, Schulz V, Knorre W A, Pohl H D, Korz D, Sanders E A, Ross A, Deckwer W D: High cell density cultivation of Escherichia coli at controlled specific growth rate. J Biotechnol 1991, 20(1):17-27). Purification was done using a combination of affinity (HIS and STREP tag) and size exclusion chromatography, followed by activation using thrombin, which cleaved off the affinity tags as well.

Comparative Example 4: Duration of Effect of rBoNT/A-PAS100 in a "Mouse Running Assay"

Equipotent dosages of rBoNT/A-PAS100 or Xeomin® were injected into the M. gastrocnemius of eight mice each that had been trained in a treadmill. Using these dosages, only a sub-maximum paralysis was observed in order to exclude potential systemic effects as far as possible, which may have an impact on the duration of effect. The daily running distance in the treadmill was measured over 15 days. The paralysis caused by the toxins was plotted as percentage of the running distance on the day before the injection, which was set as 100%, against the time.

The injection of rBoNT/A-PAS100 resulted in a maximum paralysis after 4 days, for the control group treated with Xeomin® maximum paralysis was observed after 4 days as well. During the recovery phase the running distance of the control group reached a value of 40% of the starting value 5 days after maximum paralysis was observed (day 9), and the same effect was observed for the group treated with rBoNT/A-PAS100. Thus, the duration of effective paralysis was essentially the same, and PASylation at the C-terminus of the heavy chain did not exert any significant effect on the duration of effect.

TABLE 1

| Sequences |
|---|
| SEQ ID NO 1:<br>ASPAAPAPASPAAPAPSAPA |
| SEQ ID NO 2:<br>AAPASPAPAAPSAPAPAAPS |
| SEQ ID NO 3:<br>APSSPSPSAPSSPSPASPSS |

TABLE 1-continued

Sequences

SEQ ID NO 4:
SAPSSPSPSAPSSPSPASPS

SEQ ID NO 5:
SSPSAPSPSSPASPSPSSPA

SEQ ID NO 6:
AASPAAPSAPPAAASPAAPSAPPA

SEQ ID NO 7:
ASAAAPAAASAAASAPSAAA

SEQ ID NO 8: PAS100 rBoNT/A-PAS100 (amino acid sequence)
SSASPAAPAPASPAAPAPSAPAASPAAPAPASPAAPAPSAPAASPAAPAP

ASPAAPAPSAPAASPAAPAPASPAAPAPSAPAASPAAPAPASPAAPAPSA

PAAPFVNKQFNYKDPVNGVDIAYIKIPNAGQMQPVKAFKIHNKIWVIPER

DTFTNPEEGDLNPPPEAKQVPVSYYDSTYLSTDNEKDNYLKGVTKLFERI

YSTDLGRMLLTSIVRGIPFWGGSTIDTELKVIDTNCINVIQPDGSYRSEE

LNLVIIGPSADIIQFECKSFGHEVLNLTRNGYGSTQYIRFSPDFTFGFEE

SLEVDTNPLLGAGKFATDPAVTLAHELIHAGHRLYGIAINPNRVFKVNTN

AYYEMSGLEVSFEELRTFGGHDAKFIDSLQENEFRLYYYNKFKDIASTLN

KAKSIVGTTASLQYMKNVFKEKYLLSEDTSGKFSVDKLKFDKLYKMLTEI

YTEDNFVKFFKVLNRKTYLNFDKAVFKINIVPKVNYTIYDGFNLRNTNLA

ANFNGQNTEINNMNFTKLKNFTGLFEFYKLLCVRGIITSKAGAGKSLVPR

GSAGAGALNDLCIKVNNWDLFFSPSEDNFTNDLNKGEEITSDTNIEAAEE

NISLDLIQQYYLTFNFDNEPENISIENLSSDIIGQLELMPNIERFPNGKK

YELDKYTMFHYLRAQEFEHGKSRIALTNSVNEALLNPSRVYTFFSSDYVK

KVNKATEAAMFLGWVEQLVYDFTDETSEVSTTDKIADITIIIPYIGPALN

IGNMLYKDDFVGALIFSGAVILLEFIPEIAIPVLGTFALVSYIANKVLTV

QTIDNALSKRNEKWDEVYKYIVTNWLAKVNTQIDLIRKKMKEALENQAEA

TKAIINYQYNQYTEEEKNNINFNIDDLSSKLNESINKAMININKFLNQCS

VSYLMNSMIPYGVKRLEDFDASLKDALLKYIYDNRGTLIGQVDRLKDKVN

NTLSTDIPFQLSKYVDNQRLLSTFTEYIKNIINTSILNLRYESNHLIDLS

RYASKINIGSKVNFDPIDKNQIQLFNLESSKIEVILKNAIVYNSMYENFS

TSFWIRIPKYFNSISLNNEYTIINCMENNSGWKVSLNYGEIIWTLQDTQE

IKQRVVFKYSQMINISDYINRWIFVTITNNRLNNSKIYINGRLIDQKPIS

NLGNIHASNNIMFKLDGCRDTHRYIWIKYFNLFDKELNEKEIKDLYDNQS

NSGILKDFWGDYLQYDKPYYMLNLYDPNKYVDVNNVGIRGYMYLKGPRGS

VMTTNIYLNSSLYRGTKFIIKKYASGNKDNIVRNNDRVYINVVVKNKEYR

LATNASQAGVEKILSALEIPDVGNLSQVVVMKSKNDQGITNKCKMNLQDN

NGNDIGFIGFHQFNNIAKLVASNWYNRQIERSSRTLGCSWEFIPVDDGWG

ERPLASPAAPAPASPAAPAPSAPAASPAAPAPASPAAPAPSAPAASPAAP

APASPAAPAPSAPAASPAAPAPASPAAPAPSAPAASPAAPAPASPAAPAP

SAPA

SEQ ID NO 9: PAS100 rBoNT/A-PAS100 (nucleic acid sequence)
TCTTCTGCAAGTCCGGCAGCACCGGCACCGGCTTCACCAGCTGCACCAGC

ACCTAGCGCACCGGCAGCATCTCCAGCAGCCCCTGCACCGGCAAGCCCTG

CAGCTCCAGCACCGTCAGCACCAGCAGCAAGCCCAGCTGCTCCTGCTCCA

GCGAGCCCAGCAGCGCCAGCTCCTAGTGCCCCTGCTGCCTCTCCTGCTGC

TCCGGCACCAGCAAGTCCTGCTGCGCCTGCACCGAGTGCTCCGGCTGCTA

GTCCTGCCGCACCAGCTCCGGCTAGTCCAGCTGCTCCAGCCCCTTCAGCC

CCTGCAGCACCATTTGTGAACAAGCAGTTTAACTATAAGGACCCGGTGAA

CGGTGTGGATATCGCGTATATCAAAATCCCGAATGCGGGCCAGATGCAAC

CAGTCAAGGCGTTCAAGATTCATAACAAGATTTGGGTTATTCCGGAACGT

GATACCTTCACCAATCCGGAAGAAGGCGATTTAAATCCGCCGCCAGAAGC

CAAACAAGTGCCGGTGAGCTACTATGATAGCACGTATCTTAGCACCGATA

ATGAAAAAGACAATTACCTGAAGGGCGTGACCAAGTTGTTCGAGCGCATC

TACAGTACCGACTTAGGCCGCATGTTGTTGACGAGCATCGTTCGCGGTAT

CCCGTTCTGGGGCGGCTCCGACCATTGATACCGAGTTGAAAGTCATTGACA

CGAACTGTATCAATGTTATCCAACCGGACGGCAGTTATCGCAGCGAGGAG

TTAAATTTGGTCATCATCGGTCCAAGCGCAGATATTATTCAGTTCGAATG

CAAGAGCTTCGGCCATGAGGTCTTGAATTTGACGCGCAACGGTTACGGCA

GCACCCAATACATCCGCTTTAGCCCGGATTTCACCTTTGGCTTCGAGGAG

AGCTTGGAGGTGGACACCAACCCGCTGTTAGGTGCCGGCAAATTCGCAAC

CGACCCGGCAGTGACGTTGGCGCACGAATTGATTCATGCGGGTCACCGCT

TATACGGTATCGCGATCAATCCGAATCGCGTCTTTAAAGTCAATACCAAC

GCGTACTACGAAATGAGCGGCTTAGAGGTTAGCTTTGAAGAATTACGCAC

CTTCGGTGGCCACGACGCCAAGTTCATCGACAGCCTGCAGGAAAATGAGT

TCCGCTTGTACTATTACAATAAATTCAAGGACATCGCGAGCACCTTAAAT

AAAGCAAAGAGCATTGTGGGCACCACCGCAAGCTTGCAGTACATGAAGAA

CGTATTTAAGGAAAAATATTTGTTGTCGGAGGATACCAGCGGGAAATTCA

GCGTCGATAAGCTGAAATTCGACAAATTGTATAAAATGCTGACCGAGATT

TACACCGAGGATAACTTCGTCAAGTTTTTTAAGGTGTTAAATCGTAAGAC

CTATTTAAACTTTGATAAAGCGGTGTTTAAAATTAATATCGTGCCGAAGG

TGAATTACACCATCTACGATGGTTTCAATTTACGCAACACGAATCTGGCG

GCGAATTTAATGGCCAAAACACCGAAATTAACAACATGAACTTTACGAA

GTTAAAGAATTTCACGGGCTTATTCGAATTCTACAAGTTATTATGCGTGC

GCGGCATCATTACCAGCAAGGCAGGTGCGGGCAAGTCCTTGGTTCCGCGT

GGCAGCGCCGGCGCCGGCGCGCTCAATGATCTGTGTATTAAAGTCAATAA

CTGGGACCTGTTCTTCAGCCCGAGCGAGGATAACTTTACCAACGACTTAA

ACAAAGGCGAGGAGATCACGAGCGATACGAACATCGAGGCGGCGGAGGAA

AATATTAGCCTGGACCTCATTCAGCAGTACTATCTGACGTTCAATTTTGA

CAATGAGCCGGAGAACATCAGCATTGAAAATCTCAGCAGCGACATCATCG

TABLE 1-continued

Sequences

GTCAGTTGGAACTGATGCCGAACATTGAACGCTTTCCGAACGGCAAAAAA
TATGAACTGGACAAGTATACCATGTTCCATTACTTACGCGCACAGGAATT
TGAGCACGGCAAGAGCCGCATTGCGCTGACCAATAGCGTTAACGAGGCCT
TGTTAAATCCGAGCCGTGTCTACACGTTCTTCAGCAGCGATTATGTCAAA
AAAGTGAACAAGGCGACCGAAGCCGCGATGTTTTTGGGCTGGGTCGAGCA
ATTGGTTTACGATTTTACCGACGAAACCAGCGAGGTGAGCACGACCGACA
AAATTGCAGATATCACCATCATCATTCCGTACATCGGTCCGGCGCTCAAT
ATCGGCAATATGTTATACAAGGACGACTTTGTGGGCGCGCTGATCTTTAG
CGGCGCGGTTATCTTATTAGAATTCATCCCGGAGATCGCAATCCCGGTCT
TGGGCACCTTTGCGTTGGTGAGCTATATCGCGAATAAAGTGCTCACGGTC
CAAACCATCGATAACGCGCTCAGCAAGCGTAATGAGAAATGGGACGAGGT
TTATAAGTATATCGTGACCAACTGGTTAGCAAAAGTCAATACGCAGATCG
ATCTCATCCGCAAAAAAATGAAAGAAGCCTTGGAAAATCAAGCGGAGGCA
ACCAAAGCCATCATTAATTACCAGTATAACCAATATACCGAAGAAGAAAA
AAACAATATCAACTTCAATATCGATGATTTGAGCAGCAAACTGAACGAGA
GCATTAACAAAGCGATGATTAACATCAACAAGTTCTTGAATCAATGCAGC
GTGAGCTATCTCATGAACAGCATGATCCCGTATGGCGTCAAACGCTTGGA
AGATTTTGACGCCAGCCTGAAAGATGCGCTCCTCAAGTATATTTATGACA
ACCGCGGCACCCTCATTGGCCAGGTGGACCGCTTGAAGGATAAAGTGAAC
AATACGCTCAGCACGGATATCCCGTTCCAGCTGAGCAAGTACGTCGACAA
CCAGCGCTTACTGAGCACCTTTACCGAGTATATCAAGAACATCATTAATA
CCAGCATCCTCAACTTGCGCTATGAGAGCAATCACCTGATCGACCTCAGC
CGCTACGCCAGCAAGATCAACATCGGCAGCAAGGTCAATTTCGACCCGAT
CGATAAGAATCAGATCCAATTGTTTAACCTGGAAAGCAGCAAGATCGAGG
TTATCTTGAAGAACGCGATTGTGTACAACAGCATGTACGAGAACTTTAGC
ACGAGCTTCTGGATTCGTATCCCGAAGTATTTCAATAGCATTAGCCTGAA
TAACGAATATACCATTATCAACTGCATGGAAAATAATAGCGGCTGGAAGG

TGAGCTTAAATTACGGCGAGATCATTTGGACCTTACAGGATACCCAAGAA
ATCAAACAGCGCGTCGTCTTTAAGTATAGCCAGATGATCAACATCAGCGA
TTACATCAACCGCTGGATCTTCGTGACCATCACCAATAATCGCTTGAATA
ATAGCAAGATTTACATCAATGGTCGCTTGATTGATCAAAAACCGATCAGC
AATCTCGGTAATATCCATGCCAGCAATAACATCATGTTTAAGTTAGACGG
TTGCCGCGATACCCACCGCTATATCTGGATCAAGTATTTTAACTTATTTG
ATAAGGAACTCAACGAAAAGGAAATTAAAGACTTATATGACAATCAGAGC
AATAGCGGCATCCTGAAGGATTTCTGGGGCGACTACCTGCAGTACGATAA
GCCGTACTATATGTTGAACTTGTATGACCCGAACAAATATGTCGATGTGA
ACAATGTGGGTATTCGTGGCTATATGTACTTAAAGGGCCCGCGTGGTAGC
GTGATGACCACGAATATTTACTTAAACAGCAGCTTATACCGCGGCACGAA
GTTTATTATCAAGAAGTATGCCAGCGGCAACAAGGACAATATCGTCCGCA
ACAACGACCGTGTGTATATTAACGTGGTGGTGAAGAATAAAGAGTACCGC
TTGGCCACGAATGCGAGCCAGGCGGGCGTGGAAAAAATCTTGAGCGCGTT
GGAGATCCCGGACGTCGGCAACCTCAGCCAGGTTGTGGTGATGAAGTCTA
AAAACGACCAGGGCATCACGAACAAGTGCAAAATGAATTTGCAAGATAAC
AACGGCAACGACATCGGCTTTATTGGTTTTCACCAGTTCAATAACATCGC
CAAACTCGTGGCCAGCAATTGGTATAACCGCCAAATTGAACGCAGCAGCC
GCACGCTCGGCTGTAGCTGGGAGTTCATCCCGGTGGACGATGGCTGGGGC
GAGCGCCCGCTCGCAAGTCCGGCAGCACCGGCACCGGCTTCACCAGCTGC
ACCAGCACCTAGCGCACCGGCAGCATCTCCAGCAGCCCCTGCACCGGCAA
GCCCTGCAGCTCCAGCACCGTCAGCACCAGCAGCAAGCCCAGCTGCTCCT
GCTCCAGCGAGCCCAGCAGCGCCAGCTCCTAGTGCCCCTGCTGCCTCTCC
TGCTGCTCCGGCACCAGCAAGTCCTGCTGCGCCTGCACCGAGTGCTCCGG
CTGCTAGTCCTGCCGCACCAGCTCCGGCTAGTCCAGCTGCTCCAGCCCCT
TCAGCCCCTGCA

---

The invention claimed is:

1. A recombinant clostridial neurotoxin comprising (i) at least two separate protein segments consisting of alanine, serine, and proline residues, wherein each of said protein segments consists of between 50 and 200 amino acid residues; or (ii) at least two separate domains having a polyproline II helix conformation, wherein each of said domains comprises an amino acid sequence consisting of between 50 and 200 amino acid residues forming said polyproline II helix conformation, and wherein a first of said protein segments or domains is inserted at the N-terminus of the light chain of said recombinant clostridial neurotoxin, and a second of said protein segments or domains is inserted at the C-terminus of the heavy chain of said recombinant clostridial neurotoxin.

2. The recombinant clostridial neurotoxin of claim 1, wherein at least one of said domains of subpart (ii) consists of alanine, serine and proline residues.

3. The recombinant clostridial neurotoxin of claim 1, wherein at least one of said protein segments or domains comprises a plurality of amino acid repeats, wherein said repeats consist of Ala, Ser, and Pro residues and wherein no more than six consecutive amino acid residues are identical.

4. The recombinant clostridial neurotoxin of claim 1, wherein at least one of said protein segments or domains comprises at least one amino acid sequence selected from the group consisting of: (a) ASPAAPAPASPAAPAPSAPA (SEQ ID NO: 1), AAPASPAPAAPSAPAPAAPS (SEQ ID NO: 2), APSSPSPSAPSSPSPASPSS (SEQ ID NO: 3), SAPSSPSPSAPSSPSPASPS (SEQ ID NO: 4), SSPSAPSSPASPSPSSPA (SEQ ID NO: 5), AASPAAPSAPPAAASPAAPSAPPA (SEQ ID NO: 6), or ASAAAPAAASAAASAPSAAA (SEQ ID NO: 7); (b) circular permuted versions of ASPAAPAPASPAAPAPSAPA (SEQ ID NO: 1), AAPASPAPAAPSAPAPAAPS (SEQ ID NO: 2), APSSPSPSAPSSPSPASPSS (SEQ ID NO: 3), SAPSSPSPSAPSSPSPASPS (SEQ ID NO: 4), SSPSAPSSPASPSPSSPA (SEQ ID NO: 5), AASPAAPSAPPAAASPAAPSAPPA (SEQ ID NO: 6), or ASAAAPAAASAAASAPSAAA (SEQ ID NO: 7); and (c) multimer(s) of ASPAAPAPASPAAPAPSAPA (SEQ ID NO: 1), AAPASPAPAAPSAPAPAAPS (SEQ ID NO: 2), APSSPSPSAPSSPSPASPSS (SEQ ID NO: 3), SAPSSPSPSAPSSPSPASPS (SEQ ID NO: 4), SSPSAPSSPASPSPSSPA (SEQ ID NO: 5), AASPAAPSAPPAAASPAAPSAPPA (SEQ ID NO: 6), or ASAAAPAAASAAASAPSAAA (SEQ ID NO: 7) as a whole or parts of these sequences.

5. The recombinant clostridial neurotoxin of claim 1, wherein the sequence of said clostridial neurotoxin is selected from the group consisting of the sequences of: *Clostridium botulinum* neurotoxin serotype A, B, C, D, E, F, G or H; the sequence of a functional variant of a *Clostridium botulinum* neurotoxin of serotype A, B, C, D, E, F, G or H; the sequence of a chimeric *Clostridium botulinum* neurotoxin, wherein the clostridial neurotoxin light chain and heavy chain are from different clostridial neurotoxin serotypes; and the sequence of a chimeric *Clostridium botulinum* neurotoxin, wherein the clostridial neurotoxin light chain and heavy chain are from different clostridial neurotoxin serotypes and wherein said recombinant clostridial neurotoxin has a light chain and a heavy chain comprised in the amino acid sequence as found in SEQ ID NO: 8.

6. The recombinant clostridial neurotoxin of claim 1 for treatment of a disease, wherein the recombinant clostridial neurotoxin causes longer lasting denervation relative to an identical clostridial neurotoxin with either one of or no said protein segments or domains.

7. A pharmaceutical composition comprising the recombinant clostridial neurotoxin of claim 1.

8. A method of cosmetic treatment of a patient comprising administering the recombinant clostridial neurotoxin of claim 1 to the patient.

9. A method for the generation of a recombinant clostridial neurotoxin according to claim 1, comprising the step of obtaining a recombinant nucleic acid sequence encoding a recombinant single-chain precursor clostridial neurotoxin by the insertion of one or more nucleic acid sequences each encoding one of said protein segments or domains at at least two positions into a nucleic acid sequence encoding a parental clostridial neurotoxin.

10. The method of claim 9, further comprising the step of heterologously expressing said recombinant nucleic acid sequence in a host cell wherein the host cell is a bacterial host cell or an *E. coli* host cell.

11. A recombinant single-chain clostridial neurotoxin comprising (i) at least two separate protein segments consisting of alanine, serine, and proline residues, wherein each of said protein segments consists of between 50 and 200 amino acid residues; or (ii) at least two separate domains having a polyproline II helix conformation, wherein each of said domains comprises an amino acid sequence consisting of between 50 and 200 amino acid residues forming said polyproline II helix conformation, which is a precursor for the recombinant clostridial neurotoxin of claim 1, optionally wherein the sequence of said clostridial neurotoxin is selected from the group consisting of the sequences of: *Clostridium botulinum* neurotoxin serotype A, B, C, D, E, F, G or H; the sequence of a functional variant of a *Clostridium botulinum* neurotoxin of serotype A, B, C, D, E, F, G or H; and the sequence of a chimeric *Clostridium botulinum* neurotoxin, wherein the clostridial neurotoxin light chain and heavy chain are from different clostridial neurotoxin serotypes.

12. A nucleic acid sequence encoding the recombinant single-chain clostridial neurotoxin of claim 11, optionally wherein the nucleic acid sequence is as found in SEQ ID NO:9.

13. A vector comprising the nucleic acid sequence of claim 12.

14. A recombinant host cell comprising the nucleic acid sequence of claim 12.

15. A method for producing the recombinant single-chain precursor clostridial neurotoxin of claim 11, comprising the step of expressing a nucleic acid sequence encoding the recombinant single-chain clostridial neurotoxin of claim 11, optionally wherein the nucleic acid sequence is as found in SEQ ID NO:9, in a recombinant host cell.

16. The recombinant clostridial neurotoxin of claim 3, wherein the proline residues comprised in said protein segment or domain constitute more than 4% and less than 40% of the amino acids of said protein segment or domain.

17. The recombinant clostridial neurotoxin of claim 4 wherein said protein segment or domain comprises (ASPAAPAPASPAAPAPSAPA)$_n$, with n being:
  a. (i) an integer selected from 3 to 25 (SEQ ID NO: 10),
     (ii) an integer selected from 4 to 8 (SEQ ID NO: 11),
     (iii) an integer selected from 5 to 10 (SEQ ID NO: 12),
     (iv) wherein n is 5 (SEQ ID NO: 13) or
     (v) wherein n is 10 (SEQ ID NO: 14);
     or
  b. (i) wherein n is an integer selected from 5 to 150 (SEQ ID NO: 15),
     (ii) wherein n is an integer selected from 6 to 20 (SEQ ID NO: 16),
     (iii) wherein n is an integer selected from 7 to 13 (SEQ ID NO: 17),
     (iv) wherein n is an integer selected from 8 to 12 (SEQ ID NO: 18), or
     (v) wherein n is an integer selected from 9 to 11 (SEQ ID NO: 19).

* * * * *